United States Patent [19]
Godfrey et al.

[11] Patent Number: 6,156,878
[45] Date of Patent: *Dec. 5, 2000

[54] LIGAND (ACT-4-L) TO A RECEPTOR ON THE SURFACE OF ACTIVATED CD4+T-CELLS

[75] Inventors: Wayne Godfrey, White Bear Lake, Minn.; Edgar G. Engleman, Atherton; David Buck, Santa Clara, both of Calif.

[73] Assignees: The Board of Trustees of the Leland Stanford Junior University, Palo Alto, Calif.; Becton Dickinson and Company, Franklin Lakes, N.J.

[ * ] Notice: This patent is subject to a terminal disclaimer.

[21] Appl. No.: 08/881,033

[22] Filed: Jun. 23, 1997

Related U.S. Application Data

[63] Continuation of application No. 08/195,967, Feb. 10, 1994.
[51] Int. Cl.$^7$ .................................................. C07K 14/705
[52] U.S. Cl. ........................................... 530/350; 530/300
[58] Field of Search .................................... 530/350, 300, 530/324, 325, 326, 327, 328, 329, 330

[56] References Cited

U.S. PATENT DOCUMENTS

| | | | |
|---|---|---|---|
| 5,329,028 | 7/1994 | Ashkenazi et al. | 548/548 |
| 5,376,367 | 12/1994 | Williams | 424/85.2 |
| 5,457,035 | 10/1995 | Baum et al. | 435/69.5 |
| 5,821,332 | 10/1998 | Godfrey et al. | 530/350 |

FOREIGN PATENT DOCUMENTS

| | | |
|---|---|---|
| 90/15076 | 12/1990 | WIPO . |
| 92/11870 | 7/1992 | WIPO . |

OTHER PUBLICATIONS

Bazan, "Emerging Families of Cytokines and Receptors," *Current Biology*, 3(9):603–606 (1993).

Dörken et al., "Leukocyte Typing IV. White Cell differentiation Antigens," (W. Knapp, Ed.) Oxford University Press: Oxford, pp. 391,396,398,409,461,474,475,477,482,485,487,488,496, 501,504 (1989).

Godfrey et al., "Molecular Clonin of a cDNA Encoding the Human Homolog of the Rat OX–40 Antigen," *Tissue Antigens* Abst. (Oct. 1993).

Mallet et al., "Characterization of the MRC OX40 Antigen of Activated CD4 Positive T Lymphocytes—A Molecule Related to Nerve Growth Factor Receptor," *EMBO J.*, 9(4):1063–1068 (1990).

Mallet et al., "A New Superfamily of Cell Surface Proteins Related to the Nerve Growth Factor Receptor," *Immunology Today*, 12:220–223 (1990).

Miura et al., "Molecular Cloning and Characterization of a Novel Glycoprotein, gp34, That Is Specifically Induced by the Human T–Cell Leukemia Virus Type I Transactivator p40$^{tax}$," *Mol. And Cell. Biol.*, 11(3):1313–1325 (1991).

Picker et al., "Control of Lymphocyte Recirculation in Man. I. Differential Regulation of the Peripheral Lymph Node Homing Receptor L–Selectin on T Cells During the Virgin to Memory Cell Transition," *J. Of Immunology*, 150(3):1105–1121 (1993).

Picker et al., "Control of Lymphocyte Recirculation in Man. II. Differential Regulation of the Cutaneous Lymphocyte-–Associated Antigen, A Tissue–Selective Homing Receptor for Skin–Homing T Cells," *J. Of Immunology*, 150(3):1122–1136 (1993).

Tanaka et al., "A Glycoprotein Antigen Detected with New Monoclonal Antibodies on the Surface of Human Lymphocytes Infected with Human T–cell Leukemia Virus Type–I (HTLV–I)," *Int. J. Cancer*, 36:549–555 (1985).

Tozawa et al., "Species–Dependent Antigenicity of the 34–kDa Glycoprotein Found on the Membrane of Various Primate Lymphocytes Transformed by Human T–Cell Leukemia Virus Type–I (HTLV–I) and Simian T–Cell Leukemia Virus (STLV–I)," *Int. J. Cancer*, 41:231–238 (1988).

Fraser et al., "Ligand–Induced Association Between the T–Cell Antigen Receptor and Two Glycoproteins," *PNAS, USA*, 86:7133–7137 (1989).

Bowie et al., "Deciphering the Message in Protein Sequences: Tolerance to Amino Acid Substitutions" *Science*, 247:1306–1310 (1990).

*Primary Examiner*—Elizabeth Kemmerer
*Attorney, Agent, or Firm*—Flehr Hohbach Test Albritton & Herbert LLP

[57] ABSTRACT

The invention provides ligands and fragments thereof to a receptor on the surface of activated CD4+ T-cells. An exemplary ligand is designated ACT-4-L-h-1. Preferred fragments include purified extracellular domains of ligands. The invention also provides humanized and human antibodies to the ligand. The invention further provides methods of using the ligand and the antibodies in treatment of diseases and conditions of the immune system. The invention also provides methods of monitoring activated CD4+ T-cells using the ligands or fragments thereof.

6 Claims, 10 Drawing Sheets

Fig.5.

```
                                      27                                                54
        CA GCA GAG ACG AGG ATG TGC GTG GGG GCT CGG CGG CTG GGC CGC GGG CCG TGT
              A   E   T   R   M   C   V   G   A   R   R   L   G   R   G   P   C
                                                              signal sequence
                                      81                                               108
        GCG GCT CTG CTC CTC CTG GGC CTG GGG CTG AGC ACC GTG ACG GGG CTC CAC TGT
         A   A   L   L   L   L   G   L   G   L   S   T   V   T   G   L   H   C
                                           ↑       ↑ cleavage
                                     135                                               162
        GTC GGG GAC ACC TAC CCC AGC AAC GAC CGG TGC TGC CAC GAG TGC AGG CCA GGC
         V   G   D   T   Y   P   S   N   D   R   C   C   H   E   C   R   P   G 189                                               216
        AAC GGG ATG GTG AGC CGC TGC AGC CGC TCC CAG AAC ACG GTG TGC CGT CCG TGC
         N   G   M   V   S   R   C   S   R   S   Q   N   T   V   C   R   P   C 243                                               270
        GGG CCG GGC TTC TAC AAC GAC GTG GTC AGC TCC AAG CCG TGC AAG CCC TGC ACG
         G   P   G   F   Y   N   D   V   V   S   S   K   P   C   K   P   C   T 297                                               324
        TGG TGT AAC CTC AGA AGT GGG AGT GAG CGG AAG CAG CTG TGC ACG GCC ACA CAG
         W   C   N   L   R   S   G   S   E   R   K   Q   L   C   T   A   T   Q 351                                               378
        GAC ACA GTC TGC CGC TGC CGG GCG GGC ACC CAG CCC CTG GAC AGC TAC AAG CCT
         D   T   V   C   R   C   R   A   G   T   Q   P   L   D   S   Y   K   P 405                                               432
        GGA GTT GAC TGT GCC CCC TGC CCT CCA GGG CAC TTC TCC CCA GGC GAC AAC CAG
         G   V   D   C   A   P   C   P   P   G   H   F   S   P   G   D   N   Q 459                                               486
        GCC TGC AAG CCC TGG ACC AAC TGC ACC TTG GCT GGG AAG CAC ACC CTG CAG CCG
         A   C   K   P   W   T  [N   C   T]  L   A   G   K   H   T   L   Q   P
                                      gly
                                     513                                               540
        GCC AGC AAT AGC TCG GAC GCA ATC TGT GAG GAC AGG GAC CCC CCA GCC ACG CAG
         A   S  [N   S   S]  D   A   I   C   E   D   R   D   P   P   A   T   Q
                  gly
                                     567                                               594
        CCC CAG GAG ACC CAG GGC CCC CCG GCC AGG CCC ATC ACT GTC CAG CCC ACT GAA
         P   Q   E   T   Q   G   P   P   A   R   P   I   T   V   Q   P   T   E
```

Fig.5(Cont).

```
                                    621                                                             648
GCC TGG CCC AGA ACC TCA CAG GGA CCC TCC ACC CGG CCC GTG GAG GTC CCC GGG
 A   W   P   R   T   S   Q   G   P   S   T   R   P   V   E   V   P   G 675                                             702
GGC CGT GCG GTT GCC GCC ATC CTG GGC CTG GGC CTG GTG CTG GGG CTG CTG GGC
 G   R   A   V   A   A   I   L   G   L   G   L   V   L   G   L   L   G
                                                                          TM
                                            729
CCC CTG GCC ATC CTG CTG GCC CTG TAC CTG CTC CGG AGG GAC CAG AGG CTG CCC
 P   L   A   I   L   L   A   L   Y   L   L   R   R   D   Q   R   L   P 783                                                     810
CCC GAT GCC CAC AAG CCC CCT GGG GGA GGC AGT TTC CGG ACC CCC ATC CAA GAG
 P   D   A   H   K   P   P   G   G   G   S   F   R   T   P   I   Q   E 837                                                     864
GAG CAG GCC GAC GCC CAC TCC ACC CTG GCC AAG ATC TGA CCT GGG CCC ACC AAG
 E   Q   A   D   A   H   S   T   L   A   K   I   *
                                                  stop
                                            891                                                     918
GTG GAC GCT GGG CCC CGC CAG GCT GGA GCC CGG AGG GTC TGC TGG GCG AGC AGG 945                                                     972
GCA GGT GCA GGC CGC CTG CCC CGC CAC GCT CCT GGG CCA ACT CTG CAC CGT TCT 999                                                    1026
AGG TGC CGA TGG CTG CCT CCG GCT CTC TGC TTA CGT ATG CCA TGC ATA CCT CCT 1053
GCC CCG CGG GAC CAC AAT AAA AAC CTT GGC AG
                          Poly-A
```

Fig. 7.
Expression of ACT-4-h-1 in Stable Cell Lines
cos-7 act4 — irrelevant PE / L106 PE
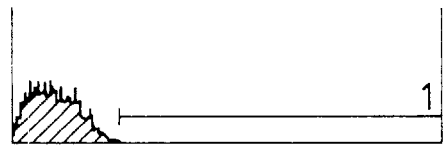
Jurkat act4 — irrelevant PE / C106 PE
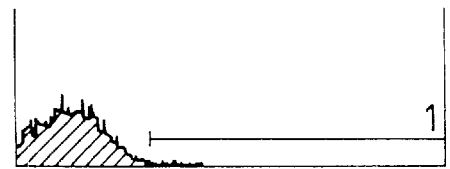
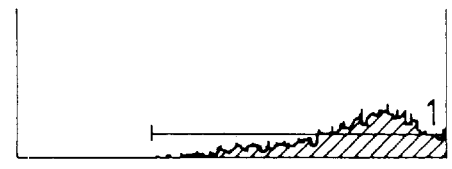
SP2/0 act4 — irrelevant PE / L106 PE ACT-4-Ig

Fig.10.

```
ggccctgggacctttgcctattttctgattgataggctttgtcttttgttttgtcttttctgggaaacttca                    78 gttttatcgcacgttccccttttccatatcttccctctaccagattgtgagatgaaggtccaacccc                         156
                                           M  E  R  V  Q  P  L tggaagagaatgtggggaatgcagccaggccaagattcgagaggaacaagctattgctgtggcctctgtaattcagg               234
 E  E  N  V  G  N  A  A  R  P  R  F  E  R  N  K  |L  L  V  A  S  V  I  Q  G| gactggggctgctcctgtgcttcacctacactgcctgcactcttcaggtatcacatcgttcttcaggtatcctcgaa               312
|L  G  L  L  L  C  F  T  Y  I  C  L  H  F  S  A  L| Q  V  S  M  R  Y  P  R  I tcatgaagtcagaacaactcagtcatcatcaactgtgatgggttttatctctcctgaagggctacttctccc                    390
 Q  S  I  K  V  Q  F  T  E  Y  K  K  E  K  G  F  I  L  T  S  Q  K  E  D  E  I ttcaaagtatcaagtcagaacaactcagtcatcatcaactgtgatgggttttatctctcctgaagggctacttctccc             468
 M  K  V  Q |N  N  S| V  I  I  N  C  D  D  G  F  Y  L  I  S  L  K  G  Y  F  S  Q
             CHO aggaagtcaacattagccttcattaccagaaggatgaggaccccctcttccaactgaagaaggtcaggtctgtcaact              546
 E  V |N  I  S| L  H  Y  Q  K  D  E  E  P  L  F  Q  L  K  K  V  R  S  V  N  S
       CHO
```

Fig.10(Cont).

```
cctgatggtggcctctctgacttacaagacaaagtctacttgactgtgaccactgacaatacctccctgatgact    627
 L  M  V  A  S  L  T  Y  K  D  K  V  Y  L  N  V  T  D  N  T  S  L  D  D  F
                                            CHO          CHO tccatgtgaatggcggagaactgattcttatccatcaaatcctggtgaattctgtgtcctttgagggctgatggca    702
 H  V  N  G  G  E  L  I  L  I  H  Q  N  P  G  E  F  C  V  L  * atatctaaaaccaggcaccagcatgaacaccagctgggggtggacaggcatggattcttcattgcaagtgaaggag    780 cctcccagctcagccacgtgggatgtgacagaagcagatcctggccctccccgccccaccccctcaggatatttaaa    858 acttattttatataccagttaatcttatttttctaaattgcctagccgtcacaccccaagattgcct            936 tgagcctactaggcaccttgtgagaaagaaaaatagatgcctcttcttcaagatgcattgtttctattggtcaggc   1014 aattgtcataataaacttatgtcattgaaaacgg   1048
      poly A signal
```

LIGAND (ACT-4-L) TO A RECEPTOR ON THE SURFACE OF ACTIVATED CD4+T-CELLS

This is a continuation of application Ser. No. 08/195,967 filed Feb. 10, 1994, pending.

CROSS-REFERENCE TO RELATED APPLICATION

Copending application U.S. Ser. No. 08/147,784, filed Nov. 3, 1993, describes related subject matter and is incorporated by reference in its entirety for all purposes.

TECHNICAL FIELD

This invention relates generally to the isolation and characterization of a ligand (ACT-4-L) to a receptor on the surface of activated CD4+ T-cells. This invention also provides antibodies to the ligand, and methods of using the ligand and the antibodies for monitoring and/or modulating immune responses.

BACKGROUND OF THE INVENTION

Immune responses are largely mediated by a diverse collection of peripheral blood cells termed leukocytes. The leukocytes include lymphocytes, granulocytes and monocytes. Granulocytes are further subdivided into neutrophils, eosinophils and basophils. Lymphocytes are further subdivided into T and B lymphocytes. T-lymphocytes originate from lymphocytic-committed stem cells of the embryo. Differentiation occurs in the thymus and proceeds through prothymocyte, cortical thymocyte and medullary thymocyte intermediate stages, to produce various types of mature T-cells. These subtypes include CD8+ T cells (also known as cytotoxic/suppressor T cells), which, when activated, have the capacity to lyse target cells, and CD4+ T cells (also known as T helper and T inducer cells), which, when activated, have the capacity to stimulate other immune system cell types.

Immune system responses are elicited in several differing situations. The most frequent response is as a desirable protection against infectious microorganisms. However, undesired immune response can occur following transplantation of foreign tissue, or in an autoimmune disease, in which one of a body's own antigens is the target for the immune response. Immune responses can also be initiated in vitro by mitogens or antibodies against certain receptors. In each of these situations, an immune response is transduced from a stimulating event via a complex interaction of leukocytic cell types. However, the participating cell types and nature of the interaction between cell types may vary for different stimulating events. For example, immune responses against invading bacteria are often transduced by formation of complexes between an MHC Class II receptor and a bacterial antigen, which then activate CD4+ T-cells. By contrast, immune responses against viral infections are principally transduced by formation of MHC Class I/viral antigen complexes and subsequent activation of CD8+ cells.

Over recent years, many leukocyte cell surface antigens have been identified, some of which have been shown to have a role in signal transduction. It has been found that signals may be transduced between a cell-surface receptor and either a soluble ligand or a cell-surface-bound ligand. The amino acid sequences of leukocyte surface molecules comprise a number of characteristic recurring sequences or motifs. These motifs are predicted to be related in evolution, have similar folding patterns and mediate similar types of interactions. A number of superfamilies, including the immunoglobulin and nerve growth factor receptor superfamilies, have been described. Members of the nerve growth factor receptor family include NGFR, found on neural cells; the B-cell antigen CD40; the rat OX-40 antigen, found on activated CD4+ cells (Mallet et al., EMBO J. 9:1063–1068 (1990) (hereby incorporated by reference for all purposes); two receptors for tumor necrosis factor (TNF), LTNFR-1 and TNFR-II, found on a variety of cell types; 4-1BB found on T-cells; SFV-T2, an open reading frame in Shope fibroma virus; and possibly fas, CD27 and CD30. See generally Mallet & Barclay, *Immunology Today* 12:220–222 (1990) (hereby incorporated by reference for all purposes).

The identification of cell-surface receptors has suggested new agents for suppressing undesirable immune responses such as transplant rejection, autoimmune disease and inflammation. Agents, particularly antibodies, that block receptors of immune cells from binding to soluble molecules or cell-bound receptors can impair immune responses. Ideally, an agent should block only undesired immune responses (e.g., transplant rejection) while leaving a residual capacity to effect desirable responses (e.g., responsive to pathogenic microorganisms). The immunosuppressive action of some agents, for example, antibodies against the CD3 receptor and the IL-2 receptor have already been tested in clinical trials. Although some trials have shown encouraging results, significant problems remain. First, a patient may develop an immune response toward the blocking agent preventing continued immunosuppressive effects unless different agents are available. Second, cells expressing the target antigen may be able to adapt to the presence of the blocking agent by ceasing to express the antigen, while retaining immune functions. In this situation, continued treatment with a single immunosuppressive agent is ineffective. Third, many targets for therapeutic agents are located on more than one leukocyte subtype, with the result that it is generally not possible to selectively block or eliminate the response of only specific cellular subtypes and thereby leave unimpaired a residual immune capacity for combating infectious microorganisms.

Based on the foregoing it is apparent that a need exists for additional and improved agents capable of suppressing immune responses, particularly agents capable of selective suppression. The present invention fulfills these and other needs, in part, by providing a ligand (ACT-4-L) to a receptor localized on activated human CD4+ T-lymphocytes.

SUMMARY OF THE INVENTION

The invention provides purified ACT-4-L ligand polypeptides. The polypeptides have a segment between 5–160 contiguous amino acids from the amino acid of an exemplified ACT-4-L ligand designated ACT-4-L-h-1. The polypeptides usually exhibit at least 80% sequence identity to the ACT-4-h-L-1 sequence and often share an antigenic determinant in common with the ACT-4-L-h-1 ligand. Usually, the polypeptides comprise an extracellular domain.

The invention also provides purified extracellular domains of ACT-4-L ligands. These domains comprise at least five contiguous amino acids from the full-length ACT-4-L-h-1 extracellular domain. Some of these extracellular domains are full-length. Other extracellular domains are fragments of full-length domains. Some extracellular domains specifically bind to the ACT-4-L-h-1 ligand. Other extracellular domains specifically bind to an exemplified receptor of ACT-4-L-h-1, the receptor being designated ACT-4-h-1. Some extracellular domains consist essentially of a domain possessing a particular functional property, for example, the capacity to specifically bind to the ACT-4-h-1 receptor. Some extracellular domains inhibit in vitro activation of $CD4^+$ T-cells expressing the ACT-4-h-1 receptor on their surface. Other extracellular domains stimulate in vitro activation of such T-cells. Any of the above extracellular domains may further comprise a linked second polypeptide such as the constant region of an immunoglobulin heavy chain.

The invention also provides an ACT-4 receptor polypeptide consisting essentially of a domain that specifically binds to the ACT-4-L-h-1 ligand.

The invention further provides antibodies that specifically bind to ACT-4-L-h-1, preferably to an extracellular domain thereof. Preferred antibodies are humanized antibodies and human antibodies. The antibodies have a variety of binding specificities. For example, some humanized antibodies specifically bind to the ACT-4-L-h-1 ligand on the surface of a B-cell so as to inhibit activation of the B cell. Other antibodies stimulate activation of B-cells. Other antibodies specifically bind to the ACT-4-L-h-1 ligand on the surface of a B-cell so as to inhibit the capacity of the B-cell to activate $CD4^+$ T-cells.

In another aspect, the invention provides pharmaceutical compositions. The pharmaceutical compositions comprise a pharmaceutically active carrier and an agent that specifically binds to an extracellular domain of the ACT-4-L-h-1 ligand.

The invention further provides methods of suppressing an immune response in a patient having an immune disease or condition. The methods comprise administering an effective amount of a pharmaceutical composition comprising a pharmaceutically active carrier and an agent that specifically binds to the ACT-4-L-h-1 ligand. Preferred agents are monoclonal antibodies, ACT-4-L ligand polypeptides and ACT-4 receptor polypeptides. The invention provides other methods of suppressing an immune response in which the agent competes with the ACT-4-L-h-1 ligand for specific binding to the ACT-4-h-1 receptor.

The invention also provides methods of screening for immunosuppressive agents. The methods comprise contacting an ACT-4-L-h-1 ligand polypeptide with a potential immunosuppressive agent. Specific binding between the ACT-4-L-h-1 ligand polypeptide and the agent is detected. The specific binding is indicative of immunosuppressive activity.

The invention also provides methods of monitoring activated $CD4^+$ T-cells. The methods comprise contacting a tissue sample from a patient with an ACT-4-L ligand polypeptide that specifically binds to an extracellular domain of the ACT-4-h-1 receptor. Specific binding between the ACT-4-L ligand polypeptide and the tissue sample is detected to indicate the presence of the activated $CD4^+$ T-cells.

BRIEF DESCRIPTION OF THE DRAWINGS

FIG. 1: Two-color staining of peripheral blood lymphocytes to analyze expression of ACT-4-h-1 on different cell types.

FIG. 2: Kinetics of ACT-4-h-1 expression on alloantigen-activated $CD4^+$ T-cells. MCF=Mean channel fluorescence.

FIG. 3: Kinetics of ACT-4-h-1 expression on tetanus-toxoid-activated $CD4^+$ T-cells.

FIG. 4: Kinetics of ACT-4-h-1 expression on PHA-activated $CD4^+$ T-cells.

FIG. 5: cDNA (upper (SEQ ID NO:1)) and deduced amino acid sequence (lower (SEQ ID NO:2)) of ACT-4-h-1. The Figure indicates the locations of an N-terminal signal sequence, two possible signal cleavage sites (vertical arrows), two glycosylation sites (gly), a transmembrane domain (TM), a stop codon and a poly-A signal sequence.

FIG. 6: Construction of expression vector for production of stable transfectants expressing ACT-4-h-1.

FIG. 7: FACS analysis showing expression of ACT-4-h-1 on stable transfectants of COS-7, Jurkat and SP2/O cell lines.

FIG. 8: Fusion of an ACT-4-h-1 extracellular domain with an immunoglobulin heavy chain constant region to form a recombinant globulin.

FIG. 9: Schematic topographical representation of recombinant globulin formed from fusion of an ACT-4-h-1 extracellular domain with an immunoglobulin heavy chain constant region to form a recombinant globulin.

FIG. 10: cDNA sequence (SEQ ID NO:3) and predicted amino acid sequence (SEQ ID NO:4) of ACT-4-L-h-1. Boxed regions designate a transmembrane domain, four glycosylation sites and a poly-A signal.

DEFINITIONS

Abbreviations for the twenty naturally occurring amino acids follow conventional usage (*Immunology—A Synthesis,* (E. S. Golub & D. R. Gren, eds., Sinauer Associates, Sunderland, Mass., 2nd ed., 1991) (hereby incorporated by reference for all purposes). Stereoisomers (e.g., D-amino acids) of the twenty conventional amino acids, unnatural amino acids such as α,α-disubstituted amino acids, N-alkyl amino acids, lactic acid, and other unconventional amino acids may also be suitable components for polypeptides of the present invention. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, ω-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention. Similarly, unless specified otherwise, the lefthand end of single-stranded polynucleotide sequences is the 5' end; the lefthand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the RNA transcript are referred to as "downstream sequences".

The phrase "polynucleotide sequence" refers to a single or double-stranded polymer of deoxyribonucleotide or ribonucleotide bases read from the 5' to the 3' end. It includes self-replicating plasmids, infectious polymers of DNA or RNA and non-functional DNA or RNA.

The following terms are used to describe the sequence relationships between two or more polynucleotides: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA or gene sequence given in a sequence listing, such as a polynucleotide sequence shown in FIG. 5 or FIG. 10, or may comprise a complete cDNA or gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith & Waterman, *Appl. Math.* 2:482 (1981), by the homology alignment algorithm of Needleman & Wunsch, *J. Mol. Biol.* 48:443 (1970), by the search for similarity method of Pearson & Lipman, *Proc. Natl. Acad. Sci. (USA)* 85:2444 (1988), by computerized implementations of these algorithms (FASTDB (Intelligenetics), BLAST (National Center for Biomedical Information) or GAP, BESTFIT, FASTA, and TFASTA (Wisconsin Genetics Software Package Release 7.0, Genetics Computer Group, 575 Science Dr., Madison, Wis.)), or by inspection, and the best alignment (i.e., resulting in the highest percentage of sequence similarity over the comparison window) generated by the various methods is selected. The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 70, 80 or 85 percent sequence identity, preferably at least 90 to 95 percent sequence identity, more usually at least 99 percent sequence identity as compared to a reference sequence over a comparison window of at least 20 nucleotide positions, frequently over a window of at least 25–50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a segment of the full-length ACT-4-h-1 sequence shown in FIG. 5 or a segment of the full-length ACT-4-L-h-1 sequence shown in FIG. 10.

As applied to polypeptides, the term "substantial identity" means that two peptide sequences, when optimally aligned, such as by the programs BLAZE (Intelligenetics) GAP or BESTFIT using default gap weights, share at least 70 percent or 80 percent sequence identity, preferably at least 90 percent sequence identity, more preferably at least 95 percent sequence identity or more (e.g., 99 percent sequence identity). Preferably, residue positions which are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

The term "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 to 90 percent of all macromolecular species present in the composition. Most preferably, the object species is purified to essential homogeneity (contaminant species cannot be detected in the composition by conventional detection methods) wherein the composition consists essentially of a single macromolecular species.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

The term "epitope" includes any protein determinant capable of specific binding to an immunoglobulin or T-cell receptor. Epitopic determinants usually consist of chemically active surface groupings of molecules such as amino acids or sugar side chains and usually have specific three dimensional structural characteristics, as well as specific charge characteristics.

Specific binding exists when the dissociation constant for a dimeric complex is $\leq 1\ \mu M$, preferably $\leq 100$ nM and most preferably $\leq 1$ nM.

The term "higher cognate variants" as used herein refers to a gene sequence that is evolutionarily and functionally related between humans and higher mammalian species, such as primates, porcines and bovines. The term does not include gene sequences from rodents, such as rats. Thus, the cognate primate gene to the ACT-4-h-1 gene is the primate gene which encodes an expressed protein which has the greatest degree of sequence identity to the ACT-4-h-1 receptor protein and which exhibits an expression pattern similar to that of the ACT-4-h-1 protein (i.e., expressed on activated $CD4^+$ cells). Similarly, the cognate primate gene to the ACT-4-L-h-1 gene is the gene whose expressed protein shows greatest sequence identity to the ACT-4-L-h-1 ligand protein and which exhibits a similar expression pattern (i.e., expressed on activated B-cells).

A population of cells is substantially enriched in a selected cell type when that cell type constitutes at least 30, 50 or 70% of the population.

The term "patient" includes human and veterinary subjects.

A test substance competes with a reference for specific binding to an antigen when an excess of the test substance substantially inhibits binding of the reference in a competition assay. Numerous types of competition assay including radioimmunoassay and ELISA are available. See Harlow & Lane, *Antibodies, A Laboratory Manual*, Cold Spring Harbor (1988). Substantially inhibits means that the test substance reduces specific binding of the reference usually by at least 10%, 25%, 50%, 75%, or 90%. Test substances identified by a competition assay include those binding to the same epitope as the reference and those binding to an adjacent epitope sufficiently proximal to that of the epitope bound by the reference antibody for steric hindrance to occur.

DETAILED DESCRIPTION

I. ACT-4 Receptor Polypeptides

Figure 1:
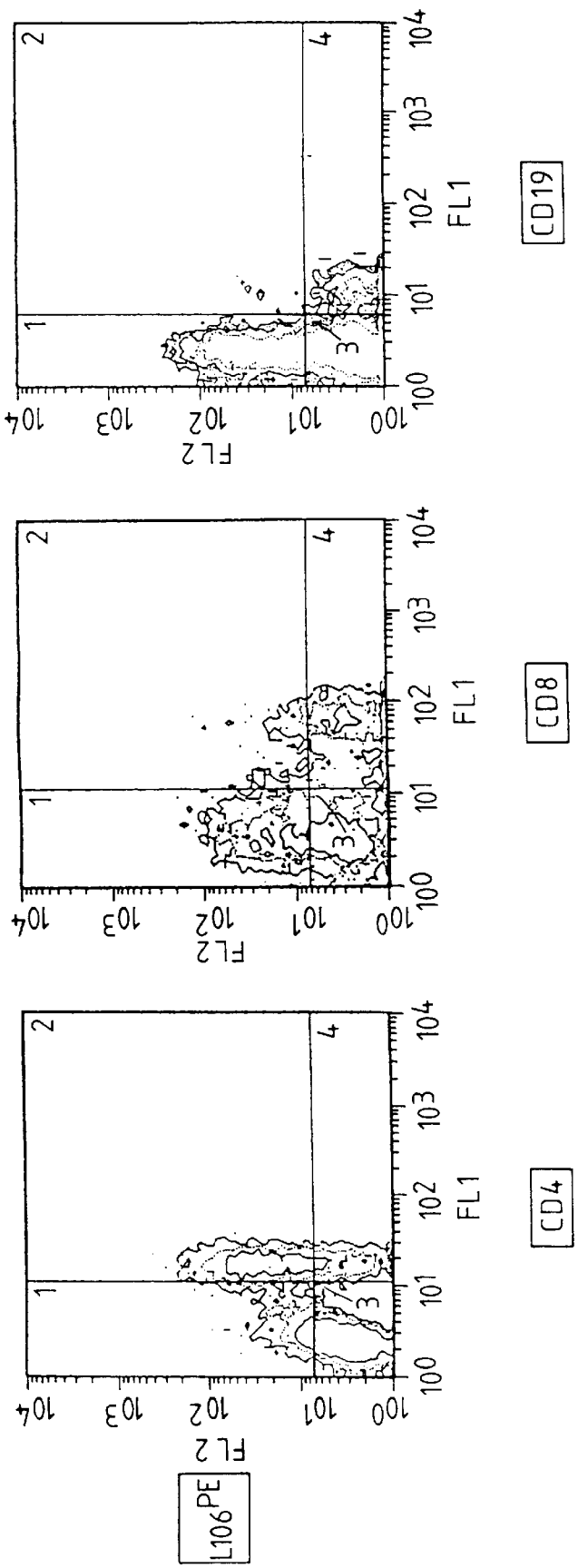

According to one embodiment of the invention, receptors on the surface of activated $CD4^+$ T-cells (referred to as ACT-4 receptors) and fragments thereof are provided. The term ACT-4 receptor polypeptide is used generically to encompass full-length proteins and fragments thereof. The term ACT-4 receptor is usually reserved for full-length proteins. The amino acid sequence of the first ACT-4 receptor to be characterized [hereinafter ACT-4-h-1] is shown in FIG. 5. The suffix -h designates human origin and the suffix -1 indicates that ACT-4-h-1 is the first ACT-4 receptor to be characterized. The term ACT-4 receptor refers not only to the protein having the sequence shown in FIG. 5, but also to other proteins that represent allelic, nonallelic, and higher cognate variants of ACT-4-h-1, and natural or induced mutants of any of these. Usually, ACT-4 receptor polypeptides will also show substantial sequence identity with the ACT-4-h-1 sequence. Typically, an ACT-4 receptor polypeptide will contain at least 4 and more commonly 5, 6, 7, 10 or 20, 50 or more contiguous amino acids from the ACT-4-h-1 sequence. It is well known in the art that functional domains, such as binding domains or epitopes can be formed from as few as four amino acids residues.

ACT-4 receptor polypeptides will typically exhibit substantial amino acid sequence identity with the amino acid sequence of ACT-4-h-1, and be encoded by nucleotide sequences that exhibit substantial sequence identity with the nucleotide sequence encoding ACT-4-h-1 shown in FIG. 5. The nucleotides encoding ACT-4 receptor proteins will also typically hybridize to the ACT-4-h-1 sequence under stringent conditions. However, these nucleotides will not usually hybridize under stringent conditions to the nucleic acid encoding OX-40 receptor, as described by Mallet et al., *EMBO J.* 9:1063–68 (1990) (hereby incorporated by reference for all purposes) (See particularly FIG. 2A of the Mallet et al. reference). Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and Ph) at which 50% of the target sequence hybridizes to a perfectly matched probe. Typically, stringent conditions will be those in which the salt concentration is at least about 0.02 molar at Ph 7 and the temperature is at least about 60° C. As other factors may significantly affect the stringency of hybridization, including, among others, base composition and size of the complementary strands, the presence of organic solvents and the extent of base mismatching, the combination of parameters is more important than the absolute measure of any one.

Usually, ACT-4 receptor polypeptides will share at least one antigenic determinant in common with ACT-4-h-1 but will not be specifically reactive with antibodies against the rat OX-40 polypeptide. The existence of a common antigenic determinant is evidenced by cross-reactivity of the variant protein with any antibody prepared against ACT-4-h-1 (see Section IV). Cross-reactivity is often tested using polyclonal sera against ACT-4-h-1, but can also be tested using one or more monoclonal antibodies against ACT-4-h-1, such as the antibody designated L106.

Often ACT-4 receptor polypeptides will contain modified polypeptide backbones. Modifications include chemical derivatizations of polypeptides, such as acetylations, carboxylations and the like. They also include glycosylation modifications (N- and O-linked) and processing variants of a typical polypeptide. These processing steps specifically include enzymatic modifications, such as ubiquitinization and phosphorylation. See, e.g., Hershko & Ciechanover, *Ann. Rev. Bioch.* 51:335–364 (1982). The ACT-4-h-1 protein, for example, is heavily modified in that the observed molecular weight is about 50 kDa, whereas the predicted molecular weight based on amino acid sequence is only 27 kDa. Two putative glycosylation sites have been identified in its extracellular domain.

ACT-4 receptors likely share some or all of the topological features found for ACT-4-h-1. The amino acid sequence for ACT-4-h-1 contains a 22 or 24 amino acid putative N-terminal signal sequence. The 24 amino acid sequence is more probably based on the criteria of von Heijne, *Nucleic Acids Res.* 14:4683–4690 (1986) (incorporated by reference for all purposes). The ACT-4-h-1 receptor contains a single additional hydrophobic stretch of 27 amino acids spanning residues 213–240. The hydrophobic stretch probably corresponds to a transmembrane domain and its existence is consistent with ACT-4-h-1 being a type I integral membrane protein (i.e., having a single transmembrane domain with the N-terminal domain comprising the extracellular region and the C-terminus comprising the intracellular region). The 189 or 191 amino acids (depending on the exact location of the signal cleavage site) of ACT-4-h-1 amino-proximal to the transmembrane segment are designated the extracellular domain, while the 37 amino acids carboxy-proximal to the transmembrane segment are designated the intracellular domain. From the amino-terminus, the extracellular domain has an $NH_2$-terminal hydrophobic putative signal sequence, and three intrachain loops formed by disulfide bonding between paired cysteine residues.

The topological arrangement of ACT-4 receptor polypeptides is similar to that of other members of the nerve growth factor receptor family, particularly to the rat OX-40 receptor. However, the other members show some divergence in the number of extracellular disulfide loops and glycosylation sites and in the size of the intracellular domain. See Mallet & Barclay, supra.

Although not all of the domains discussed above are necessarily present in all ACT-4 receptor polypeptides, an extracellular domain is expected to be present in most. Indeed, in some ACT-4 receptor polypeptides, it is possible that only an extracellular domain is present, and the natural state of such proteins is not as cell-surface bound proteins, but as soluble proteins, for example, dispersed in an extracellular body fluid. The existence of soluble variant forms has been observed for other cell surface receptors, including one member of the nerve growth factor receptor family, SFV-T2. See Mallet & Barclay, supra.

Besides substantially full-length polypeptides, the present invention provides for biologically active fragments of the polypeptides. Significant biological activities include receptor binding, antibody binding (e.g., the fragment competes with an intact ACT-4 receptor for specific binding to an antibody), immunogenicity (i.e., possession of epitopes that stimulate B or T cell responses against the fragment), and agonism or antagonism of the binding of an ACT-4 receptor polypeptide to its ligands. A segment of an ACT-4 receptor protein or a domain thereof will ordinarily comprise at least about 5, 7, 9, 11, 13, 16, 20, 40, or 100 contiguous amino acids.

Segments of ACT-4 receptor polypeptides are often terminated near boundaries of functional or structural domains. Such segments consist essentially of the amino acids responsible for a particular functional or structural property. Structural and functional domains are identified by comparison of nucleotide and/or amino acid sequence data such as is shown in FIG. 5 to public or proprietary sequence databases. Preferably, computerized comparison methods are used to identify sequence motifs or predicted protein conformation domains that occur in other proteins of known structure and/or function. Structural domains include an intracellular domain, transmembrane domain, and extracellular domain, which is in turn contains three disulfide-bonded loops. Functional domains include an extracellular binding domain through which the ACT-4 receptor polypeptide interacts with external soluble molecules or other cell-bound ligands and an intracellular signal-transducing domain.

Some fragments will contain only extracellular domains, such as one or more disulfide-bonded loops. Such fragments will often retain the binding specificity of an intact ACT-4 receptor polypeptide, but will be soluble rather than membrane bound. Such fragments are useful as competitive inhibitors of ACT-4 receptor binding.

ACT-4 receptors are further identified by their status as members of the nerve growth factor receptor family. The amino acid sequence of ACT-4-h-1 is at least 20% identical to NGF-R, TNF-R, CD40, 4-1BB, and fas/APO1. ACT-4-h-1 exhibits 62% amino acid sequence identity with the rat OX-40 gene, which is also characterized by selective expression on activated $CD4^+$ cells.

ACT-4 receptors are also identified by a characteristic cellular distribution. Most notably, ACT-4 receptors are usually easily detected on activated $CD4^+$ T cells (percent cells expressing usually greater than about 25 or 50% and often about 80%; mean channel fluorescence usually greater than about 10 and often about 20–25, on a Coulter Profile Flow Cytometer after immunofluorescence staining). ACT-4 receptors are usually substantially absent on resting T-cells, B-cells (unless activated with PMA), NK cells, and monocytes (unless activated with PMA). Substantially absent means that the percentage of cells expressing ACT-4 is usually less than about 5%, and more usually less than about 2%, and that the mean channel is usually less than about 4, and more usually less than about 2, measured on a Coulter Profile Flow Cytometer, after immunofluorescence staining of the cells. (See Example 2) ACT-4 receptors are usually expressed at low levels on activated $CD8^+$ cells (percent cells expressing about 4–10%; mean channel fluorescence about 2–4 on a Coulter Profile Flow Cytometer after immunofluorescence staining). The low level of expression observed on $CD8^+$ cells suggests that expression is confined to a subpopulation of $CD8^+$ cells. The expression of ACT-4 receptors on the surface of activated $CD4^+$ cells has been observed for several different mechanisms of activation, including alloantigenic, tetanus toxoid or mitogenic (e.g., PHA) stimuli. Expression peaks after about 7 days of allogantigenic or tetanus toxoid stimulation and after about three days of PHA stimulation. These data indicate that ACT-4 receptors should be classified as early activation antigens that are substantially absent on resting cells. The observation that ACT-4 receptors are preferentially expressed on activated $CD4^+$ cells and are expressed to a much lesser extent on activated $CD8^+$ cells, but are substantially absent on most or all other subtypes of lymphoid cells (except in response to highly nonphysiological stimuli such as PMA) contrasts with the cell type specificity of other activation antigens found on human leukocytes.

The expression of ACT-4 receptors on the surface of activated $CD4^+$ T cells suggests that the receptor has a role in activation of these cells. Such a roll is consistent with that of some other members of the nerve growth factor receptor family. For example, CD40 stimulates the Gl-S phase transition in B lymphocytes, and nerve growth factor receptor transduces a signal from the cytokine nerve growth factor., which results in neuronal differentiation and survival (Barde, *Neuron* 2:1525–1534 (1989)) (incorporated by reference for all purposes). However, other roles for ACT-4 receptors can also be envisaged, for example, interaction with other lymphoid cell types. The existence of such roles is consistent with the diverse functions of other nerve growth factor receptor family members, such as tumor necrosis factor, whose interaction with tumor necrosis factor receptor can result in inflammation or tumor cell death.

Fragments or analogs comprising substantially one or more functional domain (e.g., an extracellular domain) of ACT-4 receptors can be fused to heterologous polypeptide sequences, such that the resultant fusion protein exhibits the functional property(ies) conferred by the ACT-4 receptor fragment and/or the fusion partner. The orientation of the ACT-4 receptor fragment relative to the fusion partner will depend on experimental considerations such as ease of construction, stability to proteolysis, thermal stability, immunological reactivity, amino- or carboxyl-terminal residue modification, and so forth. Potential fusion partners include chromogenic enzymes such as β-galactosidase, protein A or G, a FLAG protein such as described by Blanar & Rutter, *Science* 256:1014–1018 (1992), toxins (e.g., diphtheria toxin, Psuedonomas ectotoxin A, ricin toxin or phospholipase C) and immunoglobulin components.

Recombinant globulins (Rg) formed by fusion of ACT-4 receptor fragments and immunoglobulin components often have most or all of the physiological properties associated with the constant region of the particular immunoglobulin class used. For example, the recombinant globulins may be capable of fixing complement, mediating antibody dependent cell toxicity, stimulating B cells, or traversing blood vessel walls and entering the interstitial space. The recombinant globulins are usually formed by fusing the C-terminus of an ACT-4 receptor extracellular domain to the N-terminus of the constant region domain of a heavy chain immunoglobulin, thereby simulating the conformation of an authentic immunoglobulin chain. The immunoglobulin chain is preferably of human origin, particularly if the recombinant globulin is intended for therapeutic use. Recombinant globulins are usually soluble and have a number of advantageous properties relative to unmodified ACT-4 receptors. These properties include prolonged serum half-life, the capacity to lyse target cells for which an ACT-4 receptor has affinity, by effector functions, and the capacity to bind molecules such as protein A and G, which can be used to immobilize the recombinant globulin in binding analyses.

II. Ligands to ACT-4

The invention also provides ligands that specifically bind to an ACT-4 receptor polypeptide and that are capable of forming a complex with such a polypeptide, at least in part, by noncovalent binding. The term ACT-4-L ligand polypeptide is used generically to encompass full-length proteins and fragments thereof. This term does not usually include antibodies to ACT-4 receptor polypeptides. The term ACT-4 ligand is usually used to refer to a full-length protein. Ligands can be naturally-occurring or synthetic molecules, and can be in soluble form or anchored to the surface of a cell. Multiple different ligands may bind the same ACT-4 receptor. Conversely, one ligand may bind to more than one ACT-4 receptor. Usually, binding of a ligand to an ACT-4 receptor will initiate a signal that alters the physical and/or functional phenotype of a cell bearing the ACT-4 receptor and/or a cell bearing the ACT-4 ligand. Antibodies against either ACT-4 or its ligands can have the capacity to block or stimulate signal transduction. It will, of course, be recognized that the designation of ACT-4 as a receptor and its specific binding partner(s) as ligand(s) is somewhat arbitrary and might, in some circumstances, be reversed.

Source materials for supplying ACT-4-L ligand polypeptides are identified by screening different cell types, particularly lymphoid and hematopoietic cells, bodily fluids and tissue extracts, with labelled ACT-4 receptor polypeptides, preferably in acqueous-soluble form, as a probe. Activated B cells or B cell lines may be suitable (see Example 8). HTLV-I infected T-cells are also suitable. Often, the ACT-4 receptor or a binding fragment thereof is fused or otherwise linked to a second protein for purposes of screening. Particularly suitable are recombinant globulins formed by fusing the extracellular portion of ACT-4-h-1 to the constant region of an immunoglobulin heavy chain.

ACT-4-L ligand polypeptides are purified from cells or other biological materials identified by this screening method using techniques of classical protein chemistry. Such techniques include selective precipitation with such substances as ammonium sulfate, column chromatography, immunopurification methods, and others. See, e.g., R. Scopes, *Protein Purification: Principles and Practice* (Springer-Verlag, N.Y., 1982) (incorporated by reference for all purposes). Usually, purification procedures will include an affinity chromatography step in which an ACT-4 receptor polypeptide or a binding fragment thereof is used as the immobilized reagent. ACT-4-constant regions can be conveniently immobilized by binding of the constant region moiety to protein A or G. ACT-4-L ligand polypeptides can also be purified using anti-idiotypic antibodies to ACT-4 receptors as the affinity reagent.

To determine the amino acid sequence or to obtain polypeptide fragments of a ligand, the ligand can be digested with trypsin. Peptide fragments can be separated by reverse-phase high-performance liquid chromatography (HPLC), and analyzed by gas-phase sequencing. Other sequencing methods known in the art may also be used. The sequence data can be used to design degenerate probes for isolation of cDNA or genomic clones encoding ACT-4-L ligand polypeptides.

Alternatively, cDNA clones encoding ACT-4-L ligand polypeptides can be obtained by expression cloning. In this approach, a cDNA library is prepared from cells expressing an ACT-4-L ligand polypeptides (identified as discussed, supra). The library is expressed in appropriate cells (e.g., COS-7), and clones bearing the ACT-4-L ligand polypeptide are identified by screening with labelled ACT-4 or binding fragment thereof, optionally fused to a constant domain of an immunoglobulin heavy chain.

The cDNA sequence and predicted amino acid sequence of the first ligand to an ACT-4 receptor polypeptide to be characterized are shown in FIG. 10. This ligand is designated ACT-4-L-h-1 with the suffix h designating human origin, and the suffix 1 indicating that this is the first ligand to be characterized. The coding portion of the cDNA sequence of ACT-4-L-h-1 is identical or nearly identical to that of a polypeptide termed gp34 or TA34. See Miura et al., *Mol. Cell. Biol.* 11:1313–1325 (1991) (incorporated by reference in its entirety for all purposes). The invention also includes ligands representing allelic, nonallelic, splice and higher cognate variants of ACT-4-L-h-1, and natural or induced mutants of any of these. Such variants will typically show substantial sequence identity with the ACT-4-L-h-1 sequence, and contain at least 4 and more commonly 5, 6, 7, 10 or 20, 50 or more contiguous amino acids from the ACT-4-L-h-1 sequence. Such variants will also typically be encoded by nucleotide sequences that exhibit substantial sequence identity with the nucleotide sequence encoding ACT-4-L-h-1 shown in FIG. 10. The nucleotides encoding such variants will also typically hybridize to an ACT-4-L-h-1 DNA sequence under stringent conditions. However, some such nucleotides will not hybridize under stringent conditions to DNA sequences encoding lower cognate variants (e.g. rat) of ACT-4-L-h-1. Many variants of ACT-4-L-h-1 will share at least one antigenic determinant with an ACT-4-L-h-1 ligand polypeptide as evidenced by crossreactivity with monoclonal or polyclonal antibodies against the same. However, some such variants will not crossreact with sera against lower cognate variants of ACT-4-L-h-1.

Although many ACT-4-L ligand polypeptides will show similarity to ACT-4-L-h-1 in at least one of the respects discussed above, it is entirely possible that other families of ligands exists to the ACT-4 receptor that show nothing in common with ACT-4-L-h-1 except for the capacity to specifically bind to an ACT-4 receptor. Such families of ligands are expressly included in the invention.

Often ACT-4-L ligand polypeptides will contain modifications of their backbones of the types discussed in Section I, supra. The ACT-4-L-h-1 polypeptide, for example, is heavily modified in that the observed molecular weight is about 34 kDa, whereas the predicted molecular weight based on amino acid sequence is only 21 kDa. Four putative N-linked glycosylation sites have been identified in the extracellular domain.

Many ACT-4-L ligand polypeptides likely share some or all of the topological features found for ACT-4-L-h-1. The ACT-4-L-h-1 amino acid sequence contains a putative N-terminal intracellular domain (aa 1–23), a putative hydrophobic transmembrane domain (aa 24–50) and a putative extracellular C-terminal domain (aa 51–183). This structural arrangement is consistent with ACT-4-L-h-1 being a type II integral membrane protein (i.e., having a single transmembrane domain with the C-terminal domain comprising the extracellular region and the N-terminus comprising the intracellular region).

ACT-4-L ligand polypeptides may also share some of the structural and/or functional characteristics of ligands that binds to other members of the nerve growth factor receptor superfamily. Such ligands include TNF-α, TNF-β, CO40-L, CD27-L, CD30-L. Although ACT-4-L-h-1 shows only weak primary amino acid sequence identity with TNF-α and even less similarity with other superfamily ligands, a greater similarity between all of these ligands is apparent in their predicted capacity to form higher order structures. The extracellular domains of known superfamily ligands consist of about 150 amino acids and form several β-pleated sheets, which assemble into a slitted cylindrical structure (termed a "jelly roll" by Bazan et al., *Current Biology* 3:603–606 (1993)) (incorporated by reference for all purposes). The extracellular domain of ACT-4-L-h-1 consists of 133 amino acids, and the predicted folding pattern is consistent with the formation of β-pleated sheets and a "jelly roll." Notably, all of the superfamily ligands except TNF-β also exist, in part, as type II integral membrane cell surface proteins. Superfamily ligands also exists as soluble proteins suggesting that such forms exist for ACT-4-L ligand polypeptides. The C-terminal extracellular domain of ACT-4-L-h-1 shows some sequence similarity with various dehydrogenases. Thus, some ACT-4-L ligand polypeptide may possess a dehydrogenase activity, which may play a role in intercellular signalling.

Besides substantially full-length polypeptides, the present invention provides for biologically active fragments of full-length ACT-4-L ligand polypeptides. Significant biological activities include binding to an ACT-4 receptor such as ACT-4-h-1, binding to a second ACT-4-L ligand polypeptide, antibody binding (e.g., the fragment competes with an intact ACT-4-L-h-1 ligand polypeptide for specific binding to an antibody), immunogenicity (i.e., possession of epitopes that stimulate B or T cell responses against the fragment), and agonism or antagonism of the binding of a second ACT-4-L ligand polypeptide to an ACT-4 receptor polypeptide, such as ACT-4-h-1. A segment of a full-length ACT-4-L ligand polypeptide will ordinarily comprise at least 5 contiguous amino acids, but not more than 160 contiguous amino acids from the amino acid sequence shown in FIG. 10. Often segments contain about 10, 20, 50, 75, 100 or 133 amino acids, and not more than 150 contiguous amino acids, from the sequence shown in FIG. 10.

Some fragments will contain only extracellular domains. Such fragments contain the full-length domains of naturally occurring ACT-4-L ligand polypeptides. Other fragments contain components thereof. Such fragments will often retain the binding specificity of an intact ACT-4-L ligand polypeptide, but will be soluble rather than membrane bound. Such fragments are useful as competitive inhibitors of ACT-4-L ligand polypeptide binding to a receptor.

Fragments of full-length ACT-4-L ligand polypeptides are often terminated at one or both of their ends near (i.e., within about 5, 10 or 20 aa of) the boundaries of functional or structural domains. Fragments terminated at both ends by structural or functional boundaries consist essentially of a particular segment (or domain) of ACT-4-L amino acids responsible for a functional or structural property. Structural and functional domains are identified by comparison of nucleotide and/or amino acid sequence data such as is shown in FIG. 10 to public or proprietary sequence databases. Preferably, computerized comparison methods are used to identify sequence motifs or predicted protein conformation domains that occur in other proteins of known structure and/or function. Binding domains can be identified by epitope mapping. See Section VI, infra. Structural domains include an intracellular domain, transmembrane domain, and extracellular domain. Functional domains include an extracellular binding domain through which ACT-4-L ligand polypeptides interact with external soluble molecules or cell-bound receptors and an intracellular signal-transducing domain.

Expression of ACT-4-L-h-1 and related ligands is dependent on cell type and activation status. See Example 8. Most notably, ACT-4-L-h-1 is easily detected on some PMA/ionomycin-activated B cell lines. ACT-4-L-h-1 is substantially absent on fresh resting B cells. ACT-4-L-h-1 is also expressed on HLTV-1-infected T-cells and may be infect on other T-cell types in some circumstances. See Example 8.

The affinity of an ACT-4-L ligand (expressed on activated B cells) for an ACT-4 receptor (expressed predominantly on activated CD4$^+$ cells) suggests that the interaction between ligand and receptor may have a role in activation/differentiation of CD4$^+$ T-cells and/or B cells. Both CD4$^+$ T-cell and B-cell activation are known to be multistep processes requiring antigen-specific and nonspecific stimuli. The interaction between ACT-4 and ACT-4-L would likely constitute a nonantigen-specific stimulus effective on either or both of the respective cells bearing these antigens. The stimulus might be direct when as, for example, the ligand-receptor binding triggers an enzymic activity in the intracellular domain in ligand and/or receptor, which activity in turn initiates a cascade of metabolic events in one or both of the respective cells. Alternatively, the stimulus might be indirect; for example, the interaction between ACT-4 and ACT-4-L might increase the avidity of cellular interactions between other ligand-receptor pairs or control leukocyte localization and migration. Interaction of ACT-4 and ACT-4-L may act in conjunction with binding of other $T_H$-B cell receptor/ligand pairs such as CD2/LFA-3 (Moingeon et al., *Nature* 339:314 (1988)), CD4/MHC class II (Doyle & Stominger, *Nature* 330:256–259 (1987)), LFA-1/ICAM-I/ICAM-2 (Makgoba et al., *Nature* 331:86–88 (1988) and Staunton et al., *Nature* 339:61–64 (1989)) and B7/CD28 (Linsley et al., *J. Exp. Med.* 173:721–730 (1991)). ACT-4/ACT-4-L interactions may also be enhanced or diminished by binding of soluble molecules to CD4$^+$ T-cells and/or B cells. Likely soluble molecules are cytokines including, e.g., interleukins IL-1 through IL-13, tumor necrosis factors α & β, interferons α, β and γ, tumor growth factor Beta (TGF-β), colony stimulating factor (CSF) and granulocyte monocyte colony stimulating factor (GM-CSF).

Expression of ACT-4-L ligand on certain subtypes of T-cells in some circumstances may confer additional or alternate roles for ACT-4/ACT-4-L interactions. For instance, efficiency of infection of T-cells by human immunodeficiency virus (HIV) or other viruses and pathogens may be affected by ACT-4 or ACT-4-L or by interactions between the two. In addition it is possible that ACT-4 and ACT-4-L could be expressed by the same cells (e.g., activated CD4$^+$ T-cells). In these circumstances, interactions between receptor and ligand may affect the growth and activation state of their respective cells.

Fragments or analogs comprising substantially one or more functional domain (e.g., an extracellular domain) of ACT-4-L ligand polypeptides can be fused or otherwise linked to heterologous polypeptide sequences, such that the resultant fusion protein exhibits the functional property(ies) conferred by the ACT-4-L ligand polypeptide and/or the fusion partner. Suitable fusion partners are as discussed in Section I, supra.

The ACT-4-L ligand polypeptides can be used to affinity purify respective ACT-4 receptors. ACT-4-L ligand polypeptides are also useful as agonists or antagonists of a second ACT-4-L ligand or an ACT-4 receptor, and can be used in the therapeutic methods discussed in Section VII, infra. ACT-4 ligand polypeptides are also useful in screening assays for identifying agonists and antagonists of ACT-4 and/or ACT-4-L.

III. Methods of producing polypeptides

A. Recombinant Technologies

The nucleotide and amino acid sequences of ACT-4-h-1 shown in FIG. 5, and corresponding sequences for other ACT-4 receptor variants allow production of polypeptides of full-length ACT-4 receptor polypeptides sequences and fragments thereof. Similarly, the amino acid sequence of ACT-4-L-h-1 and corresponding sequences for other ACT-4-L ligand polypeptide variants allow production of full-length and fragment ligand polypeptides. Such polypeptides may be produced in prokaryotic or eukaryotic host cells by expression of polynucleotides encoding ACT-4 or ACT-4-L, or fragments and analogs of either of these. The cloned DNA sequences are expressed in hosts after the sequences have been operably linked to (i.e., positioned to ensure the functioning of) an expression control sequence in an expression vector. Expression vectors are typically replicable in the host organisms either as episomes or as an integral part of the host chromosomal DNA. Commonly, expression vectors will contain selection markers, e.g., tetracycline resistance or hygromycin resistance, to permit detection and/or selection of those cells transformed with the desired DNA sequences (see, e.g., U.S. Pat. No. 4,704,362).

*E. coli* is one prokaryotic host useful for cloning the DNA sequences of the present invention. Other microbial hosts suitable for use include bacilli, such as *Bacillus subtilis,* and other Enterobacteriaceae, such as Salmonella, Serratia, and various Pseudomonas species. In these prokaryotic hosts, one can also make expression vectors, which will typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters will typically control expression, optionally with an operator sequence, and have ribosome binding site sequences and the like, for initiating and completing transcription and translation.

Other microbes, such as yeast, may also be used for expression. Saccharomyces is a preferred host, with suitable vectors having expression control sequences, such as promoters, including 3-phosphoglycerate kinase or other glycolytic enzymes, and an origin of replication, termination sequences and the like as desired. Insect cells (e.g., SF9) with appropriate vectors, usually derived from baculovirus, are also suitable for expressing ACT-4 receptor or ligand polypeptides. See Luckow, et al. *Bio/Technology* 6:47–55 (1988) (incorporated by reference for all purposes).

Higher eukaryotic mammalian tissue cell culture may also be used to express and produce the polypeptides of the present invention (see Winnacker, *From Genes to Clones* (VCH Publishers, NY, N.Y., 1987)) (incorporated by reference for all purposes). Eukaryotic cells are actually preferred, because a number of suitable host cell lines capable of secreting and authentically modifying human proteins have been developed in the art, and include the CHO cell lines, various COS cell lines, HeLa cells, myeloma cell lines, Jurkat cells, etc. Expression vectors for these cells can include expression control sequences, such as an origin of replication, a promoter (e.g., a HSV tk promoter or pgk (phosphoglycerate kinase) promoter), an enhancer (Queen et al., *Immunol. Rev.* 89:49 (1986)), and necessary processing information sites, such as ribosome binding sites, RNA splice sites, polyadenylation sites (e.g., an SV40 large T Ag poly A addition site), and transcriptional terminator sequences. Preferred expression control sequences are promoters derived from immunoglobulin genes, SV40, adenovirus, bovine papillomavirus, and the like. The vectors containing the DNA segments of interest (e.g., polypeptides encoding an ACT-4 receptor) can be transferred into the host cell by well-known methods, which vary depending on the type of cellular host. For example, $CaCl_2$ transfection is commonly utilized for prokaryotic cells, whereas $CaPO_4$ treatment or electroporation may be used for other cellular hosts. Vectors may exist as episome or integrated into the host chromosome.

B. Naturally Occurring ACT-4 or ACT-4-L Polypeptides

Natural ACT-4 receptor polypeptides are isolated by conventional techniques such as affinity chromatography. For example, polyclonal or monoclonal antibodies are raised against previously-purified ACT-4-h-1 and attached to a suitable affinity column by well known techniques. See, e.g., Hudson & Hay, *Practical Immunology* (Blackwell Scientific Publications, Oxford, UK, 1980), Chapter 8 (incorporated by reference for all purposes). For example, anti-ACT-4-h-1 can be immobilized to a protein-A sepharose column via crosslinking of the $F_c$ domain with a homobifunctional crosslinking agent, such as dimethyl pimelimidate. Cell extracts are then passed through the column, and ACT-4 receptor protein specifically bound by the column, eluted with, for example, 0.5 M pyrogenic acid, pH 2.5. Usually, an intact form of ACT-4 receptor is obtained by such isolation techniques. Peptide fragments are generated from intact ACT-4 receptors by chemical (e.g., cyanogen bromide) or enzymatic cleavage (e.g., V8 protease or trypsin) of the intact molecule. Naturally occurring ACT-4-L ligand polypeptides can be purified using an analogous approach except that the affinity reagent is an antibody specific for ACT-4-L-h-1.

C. Other Methods

Alternatively, ACT-4 or ACT-4-L polypeptides can be synthesized by chemical methods or produced by in vitro translation systems using a polynucleotide template to direct translation. Methods for chemical synthesis of polypeptides and in vitro translation are well known in the art, and are described further by Berger & Kimmel, *Methods in Enzymology, Volume 152, Guide to Molecular Cloning Techniques* Academic Press, Inc., San Diego, Calif., 1987).

IV. Nucleic Acids

A. Cloning ACT-4 or ACT-4-L Nucleic Acids

Example 5 presents nucleic acid sequence data for a cDNA clone of an ACT-4 receptor designated ACT-4-h-1. The sequence includes both a translated region and 3' and 5' flanking regions. This sequence data can be used to design probes with which to isolate other ACT-4 receptor genes. These genes include the human genomic gene encoding ACT-4-h-1, and cDNAs and genomic clones from higher mammalian species, and allelic and nonallelic variants, and natural and induced mutants of all of these genes. Specifically, all nucleic acid fragments encoding all ACT-4 receptor polypeptides disclosed in this application are provided. Genomic libraries of many species are commercially available (e.g., Clontech, Palo Alto, Calif.), or can be isolated de novo by conventional procedures. cDNA libraries are best prepared from activated $CD4^+$ cells, which express ACT-4-h-1 in large amounts.

The probes used for isolating clones typically comprise a sequence of about at least 24 contiguous nucleotides (or their complement) of the cDNA sequence shown in FIG. 5. For example, a full-length polynucleotide corresponding to the sequence shown in FIG. 5 can be labeled and used as a hybridization probe to isolate genomic clones from a human genomic clone library in e.g., λEMBL4 or λGEM11

(Promega Corporation, Madison, Wis.); typical hybridization conditions for screening plaque lifts (Benton & Davis, *Science* 196:180 (1978)) can be: 50% formamide, 5× SSC or SSPE, 1–5×Denhardt's solution, 0.1–1% SDS, 100–200 µg sheared heterologous DNA or tRNA, 0–10% dextran sulfate, $1\times10^5$ to $1\times10^7$ cpm/ml of denatured probe with a specific activity of about $1\times10^8$ cpm/µg, and incubation at 42° C. for about 6–36 hours. Prehybridization conditions are essentially identical except that probe is not included and incubation time is typically reduced. Washing conditions are typically 1–3×SSC, 0.1–1% SDS, 50–70° C. with change of wash solution at about 5–30 minutes. Hybridization and washing conditions are typically less stringent for isolation of higher cognate or nonallelic variants than for e.g., the human genomic clone of ACT-4-h-1.

Alternatively, probes can be used to clone ACT-4 receptor genes by methods employing the polymerase chain reaction (PCR). Methods for PCR amplification are described in e.g., *PCR Technology: Principles and Applications for DNA Amplification* (ed. H. A. Erlich, Freeman Press, NY, N.Y., 1992); *PCR Protocols: A Guide to Methods and Applications* (eds. Innis, et al., Academic Press, San Diego, Calif., 1990); Mattila et al., *Nucleic Acids Res.* 19:4967 (1991); Eckert, K. A. and Kunkel, T. A., *PCR Methods and Applications* 1:17 (1991); *PCR* (eds. McPherson et al., IRL Press, oxford); and U.S. Pat. No. 4,683,202 (each of which is incorporated by reference for all purposes).

Alternatively, synthetic polynucleotide sequences corresponding to all or part of the sequences shown in FIG. 5 may be constructed by chemical synthesis of oligonucleotides.

Nucleotide substitutions, deletions, and additions can be incorporated into the polynucleotides of the invention. Nucleotide sequence variation may result from degeneracy of the genetic code, from sequence polymorphisms of various ACT-4 receptor alleles, minor sequencing errors, or may be introduced by random mutagenesis of the encoding nucleic acids using irradiation or exposure to EMS, or by changes engineered by site-specific mutagenesis or other techniques of modern molecular biology. See Sambrook et al., *Molecular Cloning: A Laboratory Manual* (C.S.H.P. Press, NY 2d ed., 1989) (incorporated by reference for all purposes). For nucleotide sequence that are capable of being transcribed and translated to produce a functional polypeptide, degeneracy of the genetic code results in a number of nucleotide sequences that encode the same polypeptide. The invention includes all such sequences. Generally, nucleotide substitutions, deletions, and additions should not substantially disrupt the ability of an ACT-4 receptor polynucleotide to hybridize to the sequence of ACT-4-h-1 shown in FIG. 5 under stringent conditions. Typically, ACT-4 receptor polynucleotides comprise at least 25 consecutive nucleotides which are substantially identical to a naturally-occurring ACT-4 receptor sequence (e.g., FIG. 5), more usually ACT-4 receptor polynucleotides comprise at least 50 to 100 consecutive nucleotides, which are substantially identical to a naturally-occurring ACT-4 receptor sequence.

ACT-4 receptor polynucleotides can be short oligonucleotides (e.g., about 10, 15, 25, 50 or 100 contiguous bases from the ACT-h-1 sequence shown in FIG. 5), such as for use as hybridization probes and PCR (or LCR) primers. ACT-4 receptor polynucleotide sequences can also comprise part of a larger polynucleotide that includes sequences that facilitate transcription (expression sequences) and translation of the coding sequences, such that the encoded polypeptide product is produced. Construction of such polynucleotides is well known in the art and is described further in Sambrook et al., supra (C.S.H.P. Press, NY 2d ed. 1989). The ACT-4 receptor polynucleotide can be fused in frame with another polynucleotide sequence encoding a different protein (e.g., glutathione S-transferase, β-galactosidase or an immunoglobulin $F_c$ domain) for encoding expression of a fusion protein (see, e.g., Byrn et al., *Nature,* 344:667–670 (1990)) (incorporated by reference for all purposes).

Nucleic acids encoding ACT-4-L genes can be produced by an analogous approach, using the ACT-4-L-h-1 cDNA sequence shown in FIG. 10 as a starting material for probe design. ACT-4-L genes include the human genomic gene encoding ACT-4-L-h-1, allelic and nonallelic variants, higher cognate variants, and natural and induced mutants of all of these genes. Specifically, all nucleic acid fragments (genomic, cDNA or synthetic) encoding all ACT-4-L polypeptides disclosed in this application are provided. In nucleic acid fragments having mutations of naturally occurring sequences, generally the mutation will not substantially disrupt the ability of an ACT-4-L polynucleotide to hybridize to the nucleotide sequence of ACT-4-L-h-1 under stringent conditions. ACT-4-L ligand polynucleotides can be short oligonucleotides (e.g., about 10, 15, 25, 50 or 100 contiguous bases from the ACT-4-L-h-1 sequence shown in FIG. 10), such as for use as hybridization probes and PCR (or LCR) primers. ACT-4-L ligand polynucleotide sequences can also comprise part of a larger polynucleotide as discussed in connection with ACT-4 polynucleotide sequences.

V. Antibodies and Hybridomas

In another embodiment of the invention, antibodies against ACT-4 and ACT-4-L polypeptides are provided.

A. General Characteristics of Antibodies

Antibodies or immunoglobulins are typically composed of four covalently bound peptide chains. For example, an IgG antibody has two light chains and two heavy chains. Each light chain is covalently bound to a heavy chain. In turn each heavy chain is covalently linked to the other to form a "Y" configuration, also known as an immunoglobulin conformation. Fragments of these molecules, or even heavy or light chains alone, may bind antigen. Antibodies, fragments of antibodies, and individual chains are also referred to herein as immunoglobulins.

A normal antibody heavy or light chain has an N-terminal ($NH_2$) variable (V) region, and a C-terminal (—COOH) constant (C) region. The heavy chain variable region is referred to as $V_H$ (including, for example, $V_\gamma$), and the light chain variable region is referred to as $V_L$ (including $V_\kappa$ or $V_\lambda$). The variable region is the part of the molecule that binds to the antibody's cognate antigen, while the Fc region (the second and third domains of the C region) determines the antibody's effector function (e.g., complement fixation, opsonization). Full-length immunoglobulin or antibody "light chains" (generally about 25 kDa, about 214 amino acids) are encoded by a variable region gene at the N-terminus (generally about 110 amino acids) and a κ (kappa) or λ (lambda) constant region gene at the COOH-terminus. Full-length immunoglobulin or antibody "heavy chains" (generally about 50 Kd, about 446 amino acids), are similarly encoded by a variable region gene (generally encoding about 116 amino acids) and one of the constant region genes, e.g., gamma (encoding about 330 amino acids). Typically, the "$V_L$" will include the portion of the light chain encoded by the $V_L$ and/or $J_L$ (J or joining region) gene segments, and the "$V_H$" will include the portion of the heavy chain encoded by the $V_H$, and/or $D_H$ (D or diversity region) and $J_H$ gene segments. See, generally, Roitt et al., *Immunology* (2d ed. 1989), Chapter 6 and Paul, *Fundamen-*

*tal Immunology* (Raven Press, 2d ed., 1989) (each of which is incorporated by reference for all purposes).

An immunoglobulin light or heavy chain variable region consists of a "framework" region interrupted by three hypervariable regions, also called complementarity-determining regions or CDRs. The extent of the framework region and CDRs have been defined (see Kabat et al. (1987), "Sequences of Proteins of Immunological Interest," U.S. Department of Health and Human Services; Chothia et al., *J. Mol. Biol.* 196:901–917 (1987) (each of which is incorporated by reference for all purposes). The sequences of the framework regions of different light or heavy chains are relatively conserved within a species. The framework region of an antibody, that is the combined framework regions of the constituent light and heavy chains, serves to position and align the CDRs in three dimensional space. The CDRs are primarily responsible for binding to an epitope of an antigen. The CDRs are typically referred to as CDR1, CDR2, and CDR3, numbered sequentially starting from the N-terminus.

The constant region of the heavy chain molecule, also known as $C_H$, determines the isotype of the antibody. Antibodies are referred to as IgM, IgD, IgG, IgA, and IgE depending on the heavy chain isotype. The isotypes are encoded in the mu ($\mu$), delta ($\Delta$), gamma ($\gamma$), alpha ($\alpha$), and epsilon ($\epsilon$) segments of the heavy chain constant region, respectively. In addition, there are a number of $\gamma$ subtypes. There are two types of light chains, $\kappa$ and $\lambda$. The determinants of these subtypes typically reside in the constant region of the light chain, also referred to as the $C_L$ in general, and $C_\kappa$ or $C_\lambda$ in particular.

The heavy chain isotypes determine different effector functions of the antibody, such as opsonization or complement fixation. In addition, the heavy chain isotype determines the secreted form of the antibody. Secreted IgG, IgD, and IgE isotypes are typically found in single unit or monomeric form. Secreted IgM isotype is found in pentameric form; secreted IgA can be found in both monomeric and dimeric form.

B. Production of Antibodies

Antibodies which bind either an ACT-4 receptor, an ACT-4-L ligand, or binding fragments of either, can be produced by a variety of means. The production of non-human monoclonal antibodies, e.g., murine, rat and so forth, is well known and may be accomplished by, for example, immunizing the animal with a preparation containing an ACT-4 receptor or its ligands, or an immunogenic fragment of either of these. Particularly, useful as immunogens are cells stably transfected with a recombinant ACT-4 or ACT-4-L gene and expressing an ACT-4 receptor or ligand thereto on their cell surface. Antibody-producing cells obtained from the immunized animals are immortalized and screened for the production of an antibody which binds to ACT-4 receptors or their ligands. See Harlow & Lane, *Antibodies, A Laboratory Manual* (C.S.H.P. NY, 1988) (incorporated by reference for all purposes). A number of murine antibodies to a protein having a substantially similar or identical primary amino acid sequence to ACT-4-L-h-1 have been discussed by Tozawa et al., *Int. J. Cancer* 41:231–238 (1988); Tanaka et al., *Int. J. Cancer* 36:549–555 (1985) (incorporated by reference in their entirety for all purposes).

Several techniques for generation of human monoclonal antibodies have also been described but are generally more onerous than murine techniques and not applicable to all antigens. See, e.g., Larrick et al., U.S. Pat. No. 5,001,065, for review (incorporated by reference for all purposes). One technique that has successfully been used to generate human monoclonal antibodies against a variety of antigens is the trioma methodology of Ostberg et al. (1983), *Hybridoma* 2:361–367, Ostberg, U.S. Pat. No. 4,634,664, and Engleman et al., U.S. Pat. No. 4,634,666 (incorporated by reference for all purposes). The antibody-producing cell lines obtained by this method are called triomas, because they are descended from three cells—two human and one mouse. Triomas have been found to produce antibody more stably than ordinary hybridomas made from human cells.

An alternative approach is the generation of humanized immunoglobulins by linking the CDR regions of non-human antibodies to human constant regions by recombinant DNA techniques. See Queen et al., *Proc. Natl. Acad. Sci. USA* 86:10029–10033 (1989) and WO 90/07861 (incorporated by reference for all purposes). The humanized immunoglobulins have variable region framework residues substantially from a human immunoglobulin (termed an acceptor immunoglobulin) and complementarity determining regions substantially from a mouse immunoglobulin, e.g., the L106 antibody (see Example 1) (referred to as the donor immunoglobulin). The constant region(s), if present, are also substantially from a human immunoglobulin. The human variable domains are usually chosen from human antibodies whose framework sequences exhibit a high degree of sequence identity with the murine variable region domains from which the CDRs were derived. The heavy and light chain variable region framework residues can be derived from the same or different human antibody sequences. The human antibody sequences can be the sequences of naturally occurring human antibodies or can be consensus sequences of several human antibodies. See Carter et al., WO 92/22653. Certain amino acids from the human variable region framework residues are selected for substitution based on their possible influence on CDR conformation and/or binding to antigen. Investigation of such possible influences is by modeling, examination of the characteristics of the amino acids at particular locations, or empirical observation of the effects of substitution or mutagenesis of particular amino acids.

For example, when an amino acid differs between a murine L106 variable region framework residue and a selected human variable region framework residue, the human framework amino acid should usually be substituted by the equivalent framework amino acid from the mouse antibody when it is reasonably expected that the amino acid:

(1) noncovalently binds antigen directly, (2) is adjacent to a CDR region, (3) otherwise interacts with a CDR region (e.g., is within about 3 Å of a CDR region), or (4) participates in the $V_L$-$V_H$ interface.

Other candidates for substitution are acceptor human framework amino acids that are unusual for a human immunoglobulin at that position. These amino acids can be substituted with amino acids from the equivalent position of the L106 antibody or from the equivalent positions of more typical human immunoglobulins.

A further approach for isolating DNA sequences which encode a human monoclonal antibody or a binding fragment thereof is by screening a DNA library from human B cells according to the general protocol outlined by Huse et al., *Science* 246:1275–1281 (1989) and then cloning and amplifying the sequences which encode the antibody (or binding fragment) of the desired specificity. The protocol described by Huse is rendered more efficient in combination with phage display technology. See, e.g., Dower et al., WO 91/17271 and McCafferty et al., WO 92/01047. Phage display technology can also be used to mutagenize CDR regions of antibodies previously shown to have affinity for ACT-4 receptors or their ligands. Antibodies having improved binding affinity are selected.

Anti-ACT-4 receptor antibodies that specifically bind to the same epitope as the L106 antibody are usually identified by a competitive binding assay. The assay has three components, an ACT-4 polypeptide (e.g., ACT-4-h-1), L106 antibody, which is usually labelled, and the antibody under test. Often the ACT-4 receptor polypeptide is immobilized to a solid support. The test antibody binds to the same epitope as the L106 antibody if it reduces the amount of L106 antibody that specifically binds to the ACT-4 receptor polypeptide. The extent of screening necessary to obtain such antibodies can be reduced by generating antibodies with a protocol in which the specific epitope bound by L106 is used as an immunogen. Antibodies binding to the same epitope as L106 may exhibit a substantially, but not completely, identical amino acid sequence to the L106 antibody, or may have an unrelated primary structure to the L106 antibody.

Anti-ACT-4 receptor antibodies having a different binding specificity than L106 (i.e., which bind to a different epitope) are identified by a complementary approach. Test antibodies are screened for failure to compete with the L106 antibody for binding to an ACT-4 receptor polypeptide. The extent of screening can be reduced by generating antibodies with a protocol in which a fragment lacking a specific epitope bound by L106 is used as an immunogen.

Antibodies having the same or different binding specificity to a selected antibody to an ACT-4-L ligand polypeptide can be identified by analogous procedures.

Antibodies having the capacity to stimulate or inhibit activation of $CD4^+$ or B cells can be identified by the screening procedures discussed in Section VI, infra. Some antibodies may selectively inhibit activation in response to some stimuli (e.g., alloantigenic but not mitogenic, or vice versa), and not to others. Some antibodies' inhibitory capacity may depend on the time after activation at which the antibody is added. Some antibodies may have the capacity to activate $CD4^+$ or B cells independently of other stimuli, whereas other antibodies may only have the capacity to augment the efficacy of another stimulus such as that provided by PHA or PMA/ionomycin.

Antibodies isolated by the above procedures can be used to generate anti-idiotypic antibodies by, for example, immunization of an animal with the primary antibody. For anti-ACT-4 receptor antibodies, anti-idiotype antibodies whose binding to the primary antibody is inhibited by ACT-4 receptors or fragments thereof are selected. Because both the anti-idiotypic antibody and the ACT-4 receptors or fragments thereof bind the primary immunoglobulin, the anti-idiotypic immunoglobulin may represent the "internal image" of an epitope and thus may substitute for the ACT-4-L ligand polypeptide. Anti-idiotypic antibodies to an ACT-4-L ligand polypeptide that can substitute for an ACT-4 receptor can be produced by an analogous approach.

C. Epitope Mapping

The epitope bound by the L106 antibody or any other selected antibody to an ACT-4 receptor is determined by providing a family of fragments containing different amino acid segments from an ACT-4 receptor polypeptide, such as ACT-4-h-1. Each fragment typically comprises at least 4, 6, 8, 10, 20, 50 or 100 contiguous amino acids. Collectively, the family of polypeptide covers much or all of the amino acid sequence of a full-length ACT-4 receptor polypeptide. Members of the family are tested individually for binding to e.g., the L106 antibody. The smallest fragment that can specifically bind to the antibody under test delineates the amino acid sequence of the epitope recognized by the antibody. An analogous approach is used to map epitopes bound by antibodies to the ACT-4 ligand polypeptides.

D. Fragments of Antibodies, and Immunotoxins

In another embodiment of the invention, fragments of antibodies against ACT-4 receptors or their ligands are provided. Typically, these fragments exhibit specific binding to the ACT-4 receptor or ligand with an affinity of at least $10^7$ M, and more typically $10^8$ or $10^9$ M. Antibody fragments include separate heavy chains, light chains Fab, Fab' $F(ab')_2$, Fabc, and Fv. Fragments are produced by recombinant DNA techniques, or by enzymic or chemical separation of intact immunoglobulins.

In another embodiment, immunotoxins are provided. An immunotoxin is a chimeric compound consisting of a toxin linked to an antibody having a desired specificity. The antibody serves as a targeting agent for the toxin. See generally Pastan et al., *Cell* 47:641–648 (1986). A toxin moiety is couple to an intact antibody or a fragment thereof by chemical or recombinant DNA techniques. Preferably, the toxin is linked to an immunoglobulin chain in the form of a contiguous protein. See, e.g., Chovnick et al., *Cancer Res.* 51:465; Chaudhary et al., *Nature* 339:394 (1989) (incorporated by reference for all purposes). Examples of suitable toxin components are listed in Section I, supra, and are reviewed in, e.g., *The Specificity and Action of Animal, Bacterial and Plant Toxins* (ed. P. Cuatrecasas, Chapman Hall, London, 1976) (incorporated by reference for all purposes).

E. Hybridomas and Other Cell Lines

All hybridomas, triomas and other cell lines producing the antibodies and their fragments discussed, supra, are expressly included in the invention. These include the hybridoma line HBL106, deposited under the Budapest Treaty at the American Type Culture Collection, Rockville, Md. 20852 as ATCC HB11483, which produces the L106 mouse antibody.

F. Uses of Antibodies

Antibodies to ACT-4 and ACT-4-L polypeptides and their binding fragments are useful for screening cDNA expression libraries, preferably containing human or primate cDNA derived from various tissues and for identifying clones containing cDNA inserts, which encode structurally-related, immunocrossreactive proteins. See Aruffo & Seed, *Proc. Natl. Acad. Sci. USA* 84:8573–8577 (1987) (incorporated by reference for all purposes). Antibodies are also useful to identify and/or purify immunocrossreactive proteins that are structurally or evolutionarily related to the native ACT-4 receptor or ACT-4-L ligand polypeptides or to fragments thereof used to generate the antibody. Diagnostic and therapeutic uses of antibodies, binding fragments thereof, immunotoxins and idiotypic antibodies are described in Section VII, infra.

VI. Screening for Agonists and Antagonists

ACT-4 and ACT-4-L polypeptides, fragments, analogs thereof, antibodies and anti-idiotypic antibodies thereto, as well as other chemical or biological agents are screened for their ability to block or enhance binding of an ACT-4 to its ligand. In addition, they are tested for their ability to stimulate or inhibit metabolic processes, such as DNA synthesis or protein phosphorylation in cells bearing either an ACT-4 receptor or an ACT-4-L ligand polypeptide anchored to their surfaces.

In some methods, the compound under test is screened for its ability to block or enhance binding of a purified binding fragment of an ACT-4 receptor (or fusion protein thereof) to a purified binding fragment of an ACT-4-L ligand polypeptide (or fusion protein thereof). In such experiments, either the receptor or ligand fragment is usually immobilized to a solid support. The test compound then competes with an ACT-4 or ACT-4-L fragment (whichever is not attached to the support) for binding to the support. Usually, either the test compound or the competing ligand or receptor is labelled.

In other methods, either or both of the ACT-4 receptor and ACT-4-L ligand polypeptide, or binding fragments of these molecules, are expressed on a cell surface. For example, an ACT-4-L ligand polypeptide may be expressed on activated B-cells and/or an ACT-4 receptor polypeptide expressed on activated CD4$^+$ T-cells. Alternatively, either the ligand or receptor can be expressed from recombinant DNA in e.g., COS-7 cells (see Example 6). In these methods, the existence of agonism or antagonism is determined from the degree of binding between an ACT-4 receptor and its ligand that occurs in the presence of the test compound. Alternatively, activity of the test compound is assayed by measurement of $^3$H-thymidine incorporation into DNA or $^{32}$P-incorporation into proteins in cells bearing an ACT-4 receptor and/or cells bearing an ACT-4-L ligand polypeptide.

Compounds that block ACT-4 or ACT-4-L polypeptide-induced DNA synthesis or protein phosphorylation are antagonists. Compounds that activate DNA synthesis or phosphorylation via interaction with an ACT-4 receptor or its ligands are agonists. Agonistic or antagonistic activity can also be determined from other functional or physical endpoints of leukocyte activation, or from clinically desirable or undesirable outcomes, such as cytolytic activity, or extravasation of leukocytes into tissues from blood vessels.

The ability of agents to agonize or antagonize T-cell proliferation in vitro can be correlated with the ability to affect the immune response in vivo. In vivo activity is typically assayed using suitable animal models such as mice or rats. To assay the effect of agents on allograft rejection, for example, potential therapeutic agents can be administered to the animals at various times before introduction of the allogeneic tissue; and the animals can be monitored for graft rejection. Suitable methods for performing the transplant and monitoring for graft rejection have been described (see, e.g., Hislop et al., *J. Thorac. Cardiovasc.* 100:360–370 (1990)) (incorporated by reference for all purposes).

VII. Therapeutic and Diagnostic Methods and Compositions

A. Diagnostic Methods

Diseases and conditions of the immune system associated with an altered abundance, or functional mutation, of an ACT-4 receptor or its mRNA, or an ACT-4-L ligand or its mRNA may be diagnosed using the probes and/or antibodies of the present invention. Detection of an ACT-4 receptor or mRNA allows activated CD4$^+$ T-cells to be distinguished from other leukocyte subtypes. For example, ACT-4 receptor can be detected using an antibody or an ACT-4-L polypeptide that specifically binds to the ACT-4 receptor. The presence of activated CD4$^+$ T-cells is indicative of a MHC class II induced immune response against, e.g., invading bacteria. Comparison of the numbers of activated CD4$^+$ cells and CD8$^+$ cells may allow differential diagnosis between bacterial and viral infections, which predominantly induce these respective activated cell types. The presence of activated CD4$^+$ cells is also indicative of undesirable diseases and conditions of the immune system, such as allograft rejection, graft versus host disease, autoimmune diseases, allergies and inflammation. The efficacy of therapeutic agents in treating such diseases and conditions can be monitored.

Detection of ACT-4-L ligand or its mRNA may indicate the presence of activated B-cells and/or signal that the appearance of activated CD4$^+$ T-cells is imminent. ACT-4-L ligand can, for example, be detected using an antibody or an ACT-4 receptor polypeptide that specifically binds to the ACT-4-L ligand. Successive detection of ACT-4-L ligand followed by ACT-4 receptor (or vice versa) can allow monitoring of a progression through different temporal stages of activation in an immune response.

Diagnosis can be accomplished by removing a cellular sample (e.g., blood sample, lymph node biopsy or tissue) from a patient. The sample is then subjected to analysis for determining: (1) the amount of expressed ACT-4 receptor or ACT-4-L ligand in individual cells of the sample (e.g., by immunohistochemical staining of fixed cells with an antibody or FACS™ analysis), (2) the amount of ACT-4 receptor or ACT-4-L ligand mRNA in individual cells (by in situ hybridization with a labelled complementary polynucleotide probe), (3) the amount of ACT-4 receptor or ACT-4-L ligand mRNA in the cellular sample by RNA extraction followed by hybridization to a labeled complementary polynucleotide probe (e.g., by Northern blotting, dot blotting, solution hybridization or quantitative PCR), or (4) the amount of ACT-4 receptor or ACT-4-L ligand in the cellular sample (e.g., by cell disruption followed by immunoassay or Western blotting of the resultant cell extract).

Diagnosis can also be achieved by in vivo administration of a diagnostic reagent (e.g., a labelled anti-ACT-4 or ACT-4-L antibody for monitoring of activated CD4$^+$ T-cells or B-cells, respectively) and detection by in vivo imaging. The concentration of diagnostic agent administered should be sufficient that the binding to those cells having the target antigen is detectable compared to the background signal. Further, it is desirable that the diagnostic reagent can be rapidly cleared from the circulatory system in order to give the best target-to-background signal ratio. The diagnostic reagent can be labelled with a radioisotope for camera imaging, or a paramagnetic isotope for magnetic resonance or electron spin resonance imaging.

A change (typically an increase) in the level of protein or mRNA of an ACT-4 receptor or ACT-4-L ligand in a cellular sample from an individual, which is outside the range of clinically established normal levels, may indicate the presence of an undesirable immune reaction in the individual from whom the sample was obtained, and/or indicate a predisposition of the individual for developing (or progressing through) such a reaction. Protein or mRNA levels may be employed as a differentiation marker to identify and type cells of certain lineages (e.g., activated CD4$^+$ cells for the ACT-4 receptor) and developmental origins. Such cell-type specific detection may be used for histopathological diagnosis of undesired immune responses.

B. Diagnostic Kits

In another aspect of the invention, diagnostic kits are provided for the diagnostic methods described supra. The kits comprise container(s) enclosing the diagnostic reagents, such as labelled antibodies against ACT-4 receptors and ACT-4-L ligands, and reagents and/or apparatus for detecting the label. Other components routinely found in such kits may also be included together with instructions for performing the diagnostic test.

C. Pharmaceutical Compositions

The pharmaceutical compositions used for prophylactic or therapeutic treatment comprise an active therapeutic agent, for example, an ACT-4 receptor, an ACT-4-L ligand, fragments thereof, and antibodies and idiotypic antibodies thereto, and a variety of other components. The preferred form depends on the intended mode of administration and therapeutic application. The compositions may also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

D. Therapeutic Methods

The therapeutic methods employ the therapeutic agents discussed above for treatment of various diseases in humans or animals, particularly vertebrate mammals. The therapeutic agents include ACT-4 receptors, binding fragments thereof, ACT-4-L ligands, binding fragments thereof, anti-ACT-4 receptor and anti-ACT-4-L ligand antibodies and anti-idiotypic antibodies thereto, binding fragments of these antibodies, humanized versions of these antibodies, immunotoxins, and other agents discussed, supra. Some therapeutic agents function by blocking or otherwise antagonizing the action of an ACT-4 receptor with its ligand. Preferred therapeutic agents compete with the ligand for binding to the receptor, or compete with the receptor for binding to the ligand. Other therapeutic agents function by killing cells bearing a polypeptide against which the agent is targeted. For example, anti-ACT-4 receptor antibodies with effector functions or which are conjugated to toxins, radioisotopes or drugs are capable of selectively killing activated $CD4^+$ T-cells. Similarly, anti-ACT-4-L ligand antibodies are capable of killing activated B cells under analogous circumstances. Selective elimination of activated cells is particularly advantageous because an undesirable immune response can be reduced or eliminated, while preserving a residual immune capacity in the form of inactivated B-cells, $CD4^+$ cells and $CD8^+$ cells to combat invading microorganisms to which a patient may subsequently be exposed. Other therapeutic agents function as agonists of the interaction between an ACT-4 receptor and ACT-4-L ligand.

1. Dosages and Methods of Administration

In therapeutic applications, a pharmaceutical composition (e.g., comprising an antibody to ACT-4-h-1 or ACT-4-L-h-1) is administered, in vivo or ex vivo, to a patient already suffering from an undesirable immune response (e.g., transplant rejection), in an amount sufficient to cure, partially arrest, or detectably slow the progression of the condition, and its complications. An amount adequate to accomplish this is defined as a "therapeutically effective dose" or "efficacious dose." Amounts effective for this use will depend upon the severity of the condition, the general state of the patient, and the route of administration, and combination with other immunosuppressive drugs, if any, but generally range from about 10 ng to about 1 g of active agent per dose, with single dosage units of from 10 mg to 100 mg per patient being commonly used. Pharmaceutical compositions can be administered systemically by intravenous infusion, or locally by injection. The latter is particularly useful for localized undesired immune response such as host versus graft rejection. For a brief review of methods for drug delivery, see Langer, *Science* 249:1527–1533 (1990) (incorporated by reference for all purposes).

In prophylactic applications, pharmaceutical compositions are administered to a patients at risk of, but not already suffering an undesired immune reaction (e.g., a patient about to undergo transplant surgery). The amount of agents to be administered is a "prophylactically effective dose," the precise amounts of which will depend upon the patient's state of health and general level of immunity, but generally range from 10 ng to 1 g per dose, especially 10 mg to 100 mg per patient.

Because the therapeutic agents of the invention are likely to be more selective and generally less toxic than conventional immunomodulating agents, they will be less likely to cause the side effects frequently observed with the conventional agents. Moreover, because some of the therapeutic agents are human protein sequences (e.g., binding fragments of an ACT-4 receptor or ACT-4 ligand or humanized antibodies), they are less likely to cause immunological responses such as those observed with murine anti-CD3 antibodies. The therapeutic agents of the present invention can be combined with each other. For example, a combination of antibodies against an ACT-4-L ligand with antibodies against an ACT-4 receptor is likely to provide a particularly effective blockade against T-cell activation. The agents of the invention can also be combined with traditional therapeutics, and can be used to lower the dose of such agents to levels below those associated with side effects. For example, other immunosuppressive agents such as antibodies to the $\alpha 3$ domain, T cell antigens (e.g., OKT4 and OKT3, CD28), B-cell antigen (B7 or B7-2), antithymocyte globulin, as well as chemotherapeutic agents such as cyclosporine, glucocorticoids, azathioprine, prednisone can be used in conjunction with the therapeutic agents of the present invention.

For destruction of a specific population of target cells, it can be advantageous to conjugate the therapeutic agents of the present invention to another molecule. For example, the agents can be joined to liposomes containing particular immunosuppressive agents, to a specific monoclonal antibody or to a cytotoxin or other modulator of cellular activity, whereby binding of the conjugate to a target cell population will result in alteration of that population. A number of protein toxins have been discussed supra. Chemotherapeutic agents include, for example, doxorubicin, daunorubicin, methotrexate, cytotoxin, and anti-sense RNA. Antibiotics can also be used. In addition, radioisotopes such as yttrium-90, phosphorus-32, lead-212, iodine-131, or palladium-109 can be used. The emitted radiation destroys the targeted cells.

2. Diseases and Conditions Amenable to Treatment

The pharmaceutical compositions discussed above are suitable for treating several diseases and conditions of the immune system.

a. Transplant Rejection

Over recent years there has been a considerable improvement in the efficiency of surgical techniques for transplanting tissues and organs such as skin, kidney, liver, heart, lung, pancreas and bone marrow. Perhaps the principal outstanding problem is the lack of satisfactory agents for inducing immunotolerance in the recipient to the transplanted allograft or organ. When allogeneic cells or organs are transplanted into a host (i.e., the donor and donee are different individual from the same species), the host immune system is likely to mount an immune response to foreign antigens in the transplant (host-versus-graft disease) leading to destruction of the transplanted tissue. $CD8^+$ cells, $CD4^+$ cells and monocytes are all involved in the rejection of transplant tissues. The therapeutic agents of the present invention are useful to block alloantigen-induced immune responses in the donee (e.g., blockage or elimination of allogen-activation of $CD4^+$ T-cells by antibodies to an ACT-4 receptor or ACT-4-L ligand) thereby preventing such cells from participating in the destruction of the transplanted tissue or organ.

b. Graft Versus Host Disease

A related use for the therapeutic agents of the present invention is in modulating the immune response involved in "graft versus host" disease (GVHD). GVHD is a potentially fatal disease that occurs when immunologically competent cells are transferred to an allogeneic recipient. In this situation, the donor's immunocompetent cells may attack tissues in the recipient. Tissues of the skin, gut epithelia and liver are frequent targets and may be destroyed during the course of GVHD. The disease presents an especially severe problem when immune tissue is being transplanted, such as in bone marrow transplantation; but less severe GVHD has also been reported in other cases as well, including heart and liver transplants. The therapeutic agents of the present invention are used to block activation of, or eliminate, the donor leukocytes (particularly activated $CD4^+$ T-cells and B-cells), thereby inhibiting their ability to lyse target cells in the host.

c. Autoimmune Diseases

A further situation in which immune suppression is desirable is in treatment of autoimmune diseases such as insulin-dependent diabetes mellitus, multiple sclerosis, stiff man syndrome, rheumatoid arthritis, myasthenia gravis and lupus erythematosus. In these disease, the body develops a cellular and/or humoral immune response against one of its own antigens leading to destruction of that antigen, and potentially crippling and/or fatal consequences. Activated $CD4^+$ T-cells are believed to play a major role in many autoimmune diseases such as diabetes mellitus. Activated B cells play a major role in other autoimmune diseases such as stiff man syndrome. Autoimmune diseases are treated by administering one of the therapeutic agents of the invention, which block activation of, and/or eliminate $CD4^+$ T-cells and/or B-cells. Optionally, the autoantigen, or a fragment thereof, against which the autoimmune disease is targeted can be administered shortly before, concurrently with, or shortly after the immunosuppressive agent. In this manner, tolerance can be induced to the autoantigen under cover of the suppressive treatment, thereby obviating the need for continued immunosuppression. See, e.g., Cobbold et al., WO 90/15152 (1990).

d. Inflammation

Inflammation represents the consequence of capillary dilation with accumulation of fluid and migration of phagocytic leukocytes, such as granulocytes and monocytes. Inflammation is important in defending a host against a variety of infections but can also have undesirable consequences in inflammatory disorders, such as anaphylactic shock, arthritis, gout and ischemia-reperfusion. Activated T-cells have an important modulatory role in inflammation, releasing interferon γ and colony stimulating factors that in turn activate phagocytic leukocytes. The activated phagocytic leukocytes are induced to express a number of specific cells surface molecules termed homing receptors, which serve to attach the phagocytes to target endothelial cells. Inflammatory responses can be reduced or eliminated by treatment with the therapeutic agents of the present invention. For example, antibodies against ACT-4 or ACT-4-L block activation of, or eliminate activated, $CD4^+$ cells, thereby preventing these cells from releasing molecules required for activation of phagocytic cell types.

e. Infectious Agents

The invention also provides methods of augmenting the efficacy of vaccines in preventing or treating diseases and conditions resulting from infectious agents. Therapeutic agents having the capacity to activate $CD4^+$ T-cells and/or B-cells (e.g., certain monoclonal antibodies against an ACT-4 or ACT-4-L ligand) are administered shortly before, concurrently with, or shortly after the vaccine containing a selected antigen. The therapeutic agent serves to augment the immune response against the selected antigen. These methods may be particularly advantageous in patients suffering from immune deficiency diseases.

f. HTLV-I Infections

Antibodies against ACT-4-h-L-1 are also useful for killing HTLV-I-infected cells. As noted above, such cells express a gp34 antigen that is identical or nearly identical to ACT-4-h-1. These methods are usually performed in vivo or ex vivo on HTLV-I-infected individuals. However, the methods are also effective for killing HTLV-I-infected HIV cells in vitro. For example, the methods are particularly useful for protecting hospital workers from infection through contact with tissue samples under analysis. The risk of HTLV-I infection can be reduced by treating the samples according to the present methods (provided of course that the samples are being tested for something other than the presence of HTLV-I).

Antibodies against ACT-4-h-L-1 and also antibodies against ACT-4-h-1 may be effective to reduce or eliminate perturbations of the immune system that have been observed in individuals suffering from HTLV-I infection. Such perturbations may result from the presence of ACT-4-h-L-1 as a surface antigen on HTLV-I infected T-cells, which would allow the infected T-cells to interact with $CD4^+$ T-cells via an ACT-4 receptor.

g. Treatment of AIDS

HIV virus is known to infect human $CD4^+$ T-cells by binding to the CD4 receptor. However, it is likely that for productive infection to occur the CD4 receptor must interact with another receptor present on the receptor of $CD4^+$ T-cells. The identification of ACT-4 as a receptor on the surface of activated T-cells suggests that ACT-4 and/or its ligand ACT-4-L may interact with CD4 and contribute to HIV infection of T-cells. If so, therapeutically effective amounts of therapeutic agents targeted against ACT-4 or ACT-4-L may be effective in aborting HIV infection and thereby treating AIDS. These therapeutic agents may also be effective for killing HIV-infected $CD4^+$ T-cells either in vivo or in vitro. In vitro methods have utility in e.g. protecting hospital workers from accidental infection as discussed above.

The following examples are offered to illustrate, but not to limit, the invention.

EXAMPLES

Example 1

A Monoclonal Antibody Against ACT-4-h-1

Mice were immunized with PHA-transformed T-lymphoblasts. Splenocytes from immunized mice were fused with SP2/O myeloma cells and hybridomas secreting antibodies specific for the T-cell clone were selected. The hybridomas were cloned by limiting dilution. A monoclonal antibody, designated L106, produced by one of the resulting hybridoma, was selected for further characterization. The L106 antibody was found to have an IgG1 isotype. A hybridoma producing the antibody, designated HBL106 has been deposited as ATCC HB11483.

Example 2

Cellular Distribution of Polypeptide Recognized by L106 Antibody

Samples containing the antibody L106 were made available to certain participants at the Fourth International Workshop and Conference on Human Leucocyte Differentiation Antigens (Vienna 1989) for the purpose of identifying tissue and cell types which bind to the L106 antibody. The data from the workshop are presented in *Leukocyte Typing IV* (ed. W, Knapp, Oxford U. Press, 1989) (incorporated by reference for all purposes) and an accompanying computer data base available from Walter R. Gilks, MRC Biostatistics Unit, Cambridge University, England. This reference reports the L106 antibody binds a polypeptide of about 50 kDa. This polypeptide was reported to be present on HUT-102 cells (a transformed T-cell line), PHA-activated peripheral blood lymphocytes, an EBV-transformed B-lymphoid cell line, and HTLV-II transformed T-cell line, PMA-activated tonsil cells, ConA- or PHA-activated PBLS, and PMA-activated monocytes. The polypeptide was reported to be substantially absent on inter alia resting basophils, endothelial cells, fibroblasts, interferon γ-activated monocytes, peripheral non-T-cells, peripheral granulocytes, peripheral monocytes, peripheral mononuclear cells, peripheral T cells, and peripheral red blood cells.

The present inventors have obtained data indicating that the 50 kDa polypeptide (hereinafter "ACT-4-h-1 receptor") is preferentially expressed on the $CD4^+$ subspecies of activated T-cells. In one series of experiments, cell-specific ACT-4-h-1 expression was analyzed on unfractionated PBLs by a two-color staining method. PBL were activated with PHA for about two days (using the culture conditions described in Example 3), and analyzed for cell-surface expression of ACT-4-h-1 on different cellular subtypes by staining with two differently-labelled antibodies (FITC and PE labels). Labels were detected by FACS™ analysis essentially as described by Picker et al., *J. Immunol.* 150:1105–1121 (1993) (incorporated by reference for all purposes). One antibody, L106, was specific for ACT-4-h-1, the other antibody was specific for a particular leukocyte subtype. FIG. 1 shows three charts in which L106 staining is shown on the Y-axis of each chart, and anti-CD4, anti-CD8 and anti-CD19 staining as the X-axes of the respective charts. For the chart stained with anti-CD4, many cells appear as double positives (i.e., express both CD4 and ACT-4-h-1). For the chart stained with anti-CD8, far fewer cells appear as double positives. For the chart stained with anti-CD19 (a B-cell marker), double-positive cells are substantially absent.

In another series of experiments expression of ACT-4-h-1 was analyzed by single-color staining on isolated cell types. Cells were stained with fluorescently labelled L106 antibody and the label was detected by FACS™ analysis. See Engleman et al., *J. Immunol.* 127:2124–2129 (1981) (incorporated by reference for all purposes). In some experiments, cells were activated by PHA stimulation for about two days (again using the culture conditions described in Example 3). The results from this experiment, together with those from the two-color staining experiment described supra, are summarized in Table 1. Table 1 shows that about 80% of activated $CD4^+$ cells expressed ACT-4-h-1 with a mean channel fluorescence of >20, irrespective whether the $CD4^+$ cells are isolated (one-color staining) or in unfractionated PBLs (two-color staining). The level of expression of ACT-4-h-1 on activated $CD8^+$ cells is much lower than on activated $CD4^+$ T-cells in the two-color staining experiment, and very much lower in the one-color staining. Thus, the extent of expression on activated $CD8^+$ cells appears to depend on whether the $CD8^+$ cells are fractionated from other PBLs before activation. In unfractionated CDS+ cells (two-color staining), about 10% of cells express ACT-4-h-1, with a mean channel fluorescence of about 4. In the fractionated cells, only about 4% of cells express ACT-4-h-1 with a mean channel fluorescence of about 2. These data suggest that ACT-4-h-1 is expressed only on a small subtype of activated $CD8^+$ cells and that this subtype is somewhat more prevalent when the $CD8^+$ cells are activated in the presence of other PBLs.

Table 1 also indicates that ACT-4-h-1 was substantially absent on all resting leukocyte subtypes tested (i.e., $CD4^+$ T-cells, $CD8^+$ T-cells, $CD19^+$ B-cells, $CD14^+$ monocytes, granulocytes and platelets), and was also substantially absent on activated B-cells and monocytes. ACT-4-h-1 was also found to be substantially absent on most tumor cell lines tested. However, Molt3, Raji and NC37 cell lines did show a low level of expression.

TABLE 1

CELL SPECIFICITY OF ACT-4-h-1 EXPRESSION

| | Expression of ACT-4-h-1 | |
|---|---|---|
| | % Cells | MCF[1] |
| Two Color Staining | | |
| $CD4^+$ T-Cells (resting) | <2 | <2 |
| $CD4^+$ T-Cells (activated)[2] | 80 | 25 |
| $CD8^+$ T-Cells (resting) | <2 | <2 |
| $CD8^+$ T-Cells (activated) | 10 | 4 |
| $CD19^+$ B-Cells (resting) | <2 | <2 |
| $CD19^+$ B-Cells (activated) | <2 | <2 |
| $CD14^+$ Monocytes (resting) | <2 | <2 |
| $CD14^+$ Monocytes (activated) | <2 | <2 |
| One Color Staining | | |
| PBLs (resting) | <2 | 3 |
| PBLs (activated) | 50 | 27 |
| $CD4^+$ (resting) | <2 | <2 |
| $CD4^+$ (activated) | 80 | 22 |
| $CD8^+$ (resting) | <2 | <2 |
| $CD8^+$ (activated) | 4 | 2 |
| Granulocytes | <2 | <2 |
| Platelets | <2 | <2 |
| Tumor Lines | | |
| Molt-4, CEM, Hut 78, H9, Jurkat | <2 | <2 |
| HPB-ALL, Sezary, T-AU | <2 | <2 |
| Molt-3 | 20 | 3 |
| B-LCL, Arent, RML, JY, KHY, PGf | <2 | <2 |
| MSAB, CESS, 9037, 9062 | <2 | <2 |
| Dandi, Ramos, Namalwa | <2 | <2 |
| Raji, NC37 | 30 | 4 |
| U937, THP-1, HL-60 | <2 | <2 |
| Kgla, K562, HEL | <2 | <2 |

[1]MCF = Mean Channel Fluorescence.
[2]Cells indicated as "activated" had been stimulated with PHA for about three days.

Example 3

Time Course of ACT-4-h-1 Expression Responsive to $CD4^+$ T-cell Activation $CD4^+$ T-cells were tested for expression of ACT-4-h-1 receptors in response to various activating stimuli. $CD4^+$ T-cells were purified from peripheral blood mononuclear cells by solid-phase immunoadsorption ("panning"). $5 \times 10^4$ $CD4^+$ T-cells were cultured with an activating agent in microtiter wells containing RPMI medium supplemented with 10% human serum. Three different activating agents were used: (1) $5 \times 10^4$ irradiated (3000 rads) monocytes, (2) PHA (1 μg/ml) and (3) tetanus toxoid (5 μg/ml). $^3$H-thymidine was added to the cultures 12–16 h before harvest. After harvest, cells were tested for the expression of cell surface antigens by incubation with various labelled antibodies (L106, anti-CD4 and anti-CD8), as described by Engleman et al., *J. Immunol.* 127:2124–2129 (1981).

Figure 2:
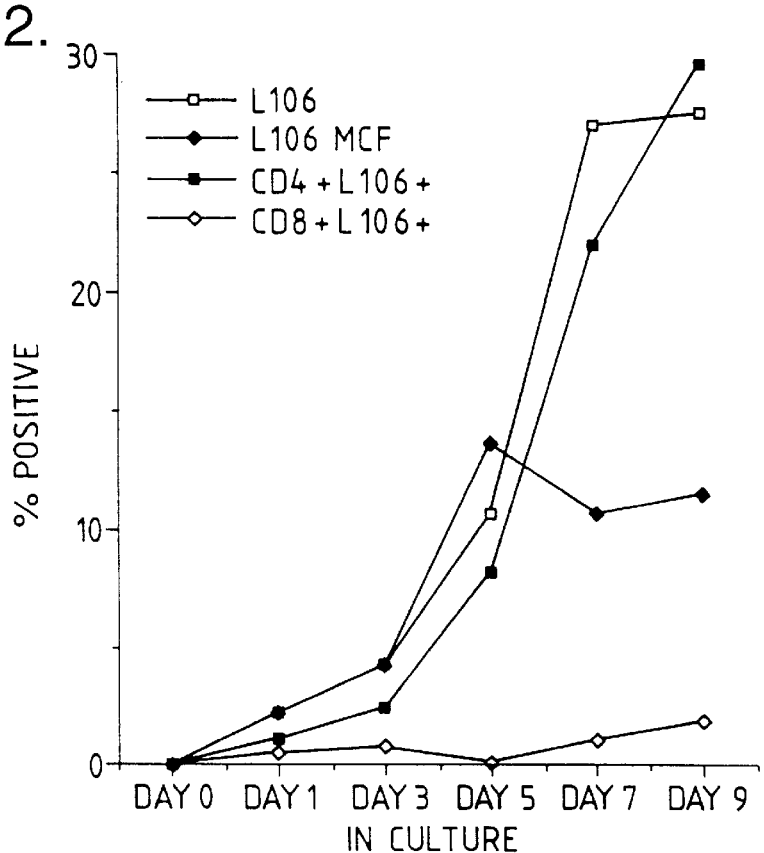
Figure 3:
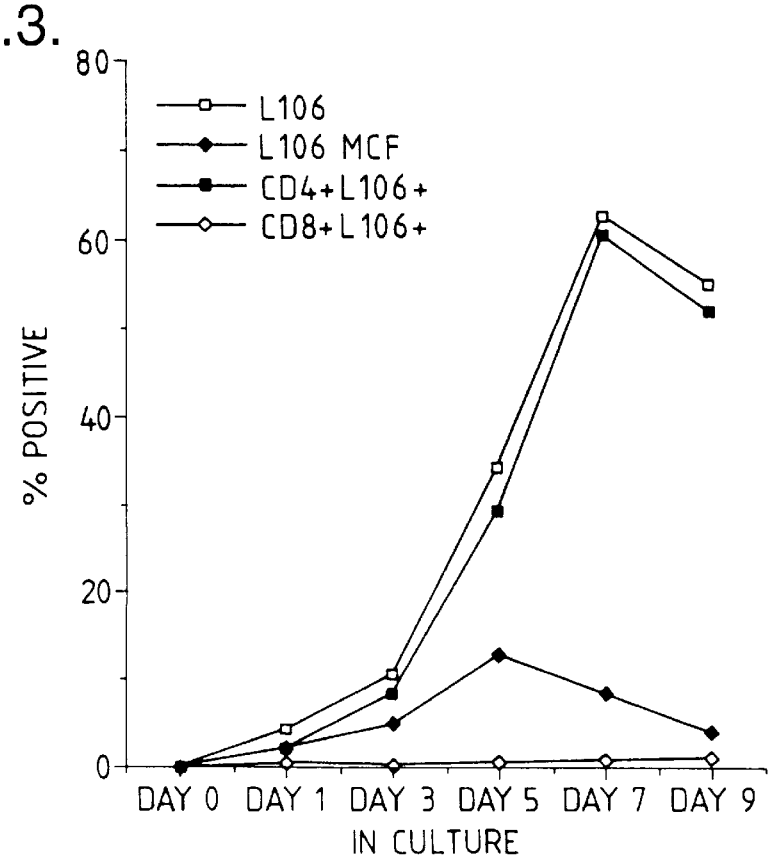
Figure 4:
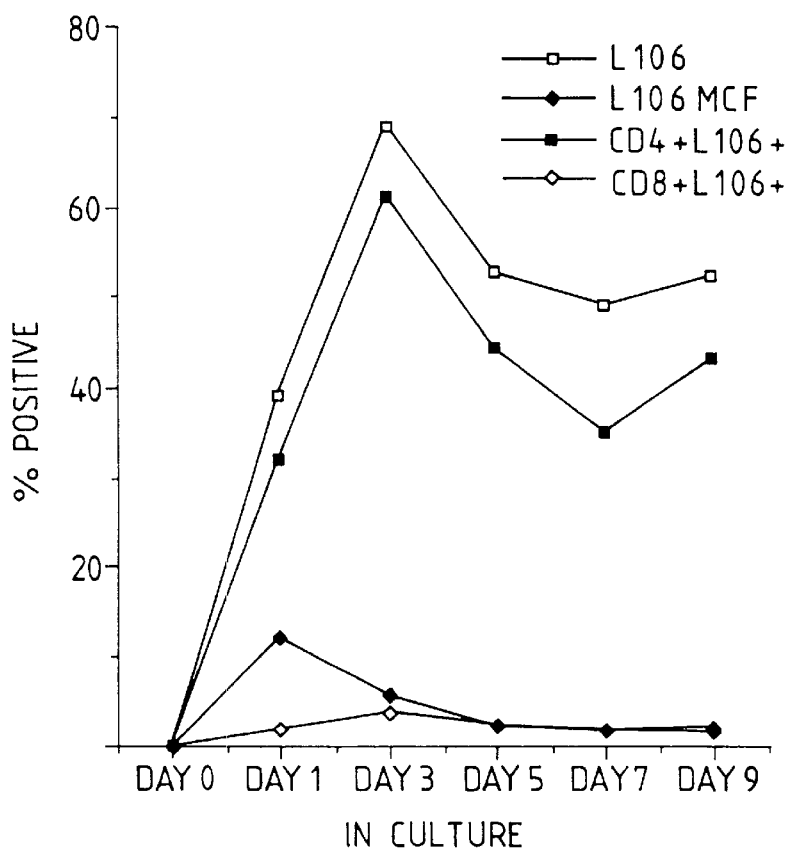

FIG. 2 shows the appearance of ACT-4-h-1 in response to alloantigen activation. Before activation, no expression was observed. The percentage of cells expressing the ACT-4-h-1 receptor increases with time, peaking at about 30% after about seven days of alloantigen activation. The results also show that essentially all cells expressing ACT-4-h-1 also expressed the CD4 receptor and that essentially no such cells expressed the CD8 receptor. FIG. 3 presents similar data for the appearance of ACT-4-h-1 in response to tetanus toxoid activation. Again, the percentage of cells expressing ACT-4-h-1 peaked at about seven days. However, at this time a higher percentage of cells (about 60%) expressed the receptor. FIG. 4 presents similar data for the appearance of ACT-4-h-1 on CD4$^+$ T-cells in response to PHA activation. In this situation, the percentage of CD4$^+$ T-cells expressing the receptor peaks at about 65% after three days of activation.

It is concluded that ACT-4-h-1 is a CD4$^+$ T-cell activation antigen that is expressed in response to diverse activating stimuli.

Example 4

Cloning ACT-4-h-1 cDNA

The cDNA clone for the ACT-4-h-1 receptor was isolated using a slightly modified COS cell expression system, first developed by Aruffo & Seed, supra. RNA was isolated from 72-hour PHA activated human peripheral blood lymphocytes. Total RNA was extracted with TRI-reagent (Molecular Research Center), and poly(A)+RNA was isolated by oligo dT-magnetic bead purification (Promega). cDNA was synthesized by the method of Gubler & Hoffman, *Gene* 25:263–369 (1982) using superscript reverse transcriptase (Gibco/BRL) and an oligo dT primer. The blunted cDNA was ligated to non-self-complementary BstXI adaptors and passed over a sephacryl S-400 spin column to remove unligated adaptors and small fragments (<300 base pairs). The linkered cDNA was then ligated into a BstXI cut eukaryotic expression vector, pcDNA-IRL, an ampicillin resistant version of pcDNA-I(Invitrogen). The precipitated and washed products of the ligation reaction were electroporated into *E. coli* strain WM1100(BioRad). Plating and counting of an aliquot of the transformed bacteria revealed a total count of 2 million independent clones in the unamplified library. Average insert size was determined to be 1.2 kb. The bulk of the library was amplified in liquid culture, 250 ml standard LB media. Plasmid was recovered by alkaline lysis and purified over an ion-exchange column (Qiagen).

Sub-confluent COS-7 cells were transfected with the purified plasmid DNA by electroporation. Cells were plated on 100 mm dishes and allowed to grow for 48 hours. Cells were recovered from the plates with PBS-EDTA solution, incubated with monoclonal antibody L106, and were panned according to standard procedures. A second round panning revealed enrichment as numerous COS cells adsorbed to the plates. Episomal DNA was recovered from the immunoselected cells by the Hirt method, and electroporated into bacteria for amplification.

Bacteria transformed with plasmid from the second round Hirt preparation were diluted into small pools of about 100 colonies. The pools were amplified and their DNA purified and tested for the ability to confer expression of the L106 antigen on COS-7 cells by immunofluorescence. Phycoerythrin-conjugated L106 antibody was used to stain COS-7 cell monolayers and the cells were then examined by manual immunofluorescence microscopy. Miniprep DNA from four out of eight pools was positive when tested for expression. The pool with the best expression, pool E, was divided into smaller pools of ~12 colonies. Three out of eight sub-pools were positive, and sub-pool E1 was plated to allow for the analysis of single colonies. Clone E1-27 was found to confer high level expression of ACT-4-h-1 receptor on the surface of transfected COS cells.

Example 5 cDNA Sequence Analysis

The insert from the clone designated E1-27 was subcloned into pBluescript and sequenced by the dideoxy chain termination method, using the T7 polymerase autoread sequencing kit (Pharmacia) on an ALF sequencer (Pharmacia). Restriction mapping revealed several convenient sites for subcloning. Five subclones were generated in pBluescript and were sequenced on both strands with M13 forward and universal primers.

The cDNA and deduced amino acid sequences of ACT-4-h-1 are shown in FIG. 5. The ACT-4-h-1 cDNA sequence of 1,137 base pairs contains a 14-bp 5' untranslated region and a 209-bp 3' untranslated region. An AATAAA polyadenylation signal is present at position 1,041 followed by an 80-bp poly A tail starting at position 1,057. The longest open reading frame begins with the first ATG at position 15 and ends with a TGA at position 846. The predicted amino acid sequence is that of a typical type 1 integral membrane protein. Hydrophobicity analysis revealed a putative signal sequence following the initiating ATG, with a short stretch of basic residues followed by a longer stretch of hydrophobic residues. A predicted signal peptide cleavage site is present at residue 22 or 24 (the latter being the more likely by the criteria of von Heijne, *Nucleic Acids Res.* 14:4683–4690 (1986)) (incorporated by reference for all purposes), leaving a mature protein of 253 amino acid residues (or 255 amino acids, if cleavage occurs at the less probable site). Hydrophobicity analysis also reveals a single large stretch of 27 hydrophobic residues predicted to be the transmembrane domain, which predicts an extracellular domain of 189 (or 191) amino acids and an intracellular domain of 37 amino acids. The extracellular domain is cysteine rich, where 18 cysteines are found within a stretch of 135 amino acids. The predicted molecular mass (Mr) for the mature protein is 27,400, and there are two potential N-glycosylation sites at amino acid residues 146 and 160.

Comparison of the amino acid sequence of ACT-4-h-1 with known sequences in the swiss-prot database using the BLAZE program reveals a sequence similarity with members of the nerve growth factor receptor superfamily. Amino acid sequences are at least 20% identical for NGF-R, TNF-R, CD40, 41-BB, and fas/APO-1,. and 62% for OX-40, allowing for gaps and deletions. Alignments of the various proteins reveal the conservation of multiple cysteine rich motifs. Three of these motifs are present in ACT-4-h-1 and OX-40, compared with four such motifs in NGF-R and CD40.

Comparison of the nucleotide sequence of ACT-4-h-1 with known sequences in the Genbank and EMBL databases using the programs BLAST and FASTDB revealed a high degree of sequence similarity with only one member of the nerve growth factor receptor family, OX-40. Allowing for gaps and insertions, the sequence identity is 66%. Comparison of the ACT-4-h-1 and OX-40 nucleotide sequences reveals that both contain a 14-bp 5' untranslated region, and both contain approximately 80-bp poly A tails. In ACT-4-h-1, however, there is a slight lengthening of the 3' untranslated region from 187-bp to 209-bp, and there is a lengthening of the coding region from 816-bp to 834-bp, a difference of 18-bp or 6 amino acid insertions. Aligning the two amino acid sequences reveals that four of the amino acid insertions occur prior to the signal sequence cleavage site. Thus, the mature ACT-4-h-1 receptor protein contains one more amino acid residue than OX-40 (i.e., 253 vs. 252 amino acids). Remarkably, the ACT-4-h-1 nucleotide sequence is much more GC rich, than the OX-40 sequence (70% v. 55%) indicating that the two sequences will not hybridize under stringent conditions.

Example 6

Production of Stable ACT-4-h-1 Transfectants

Figure 6:
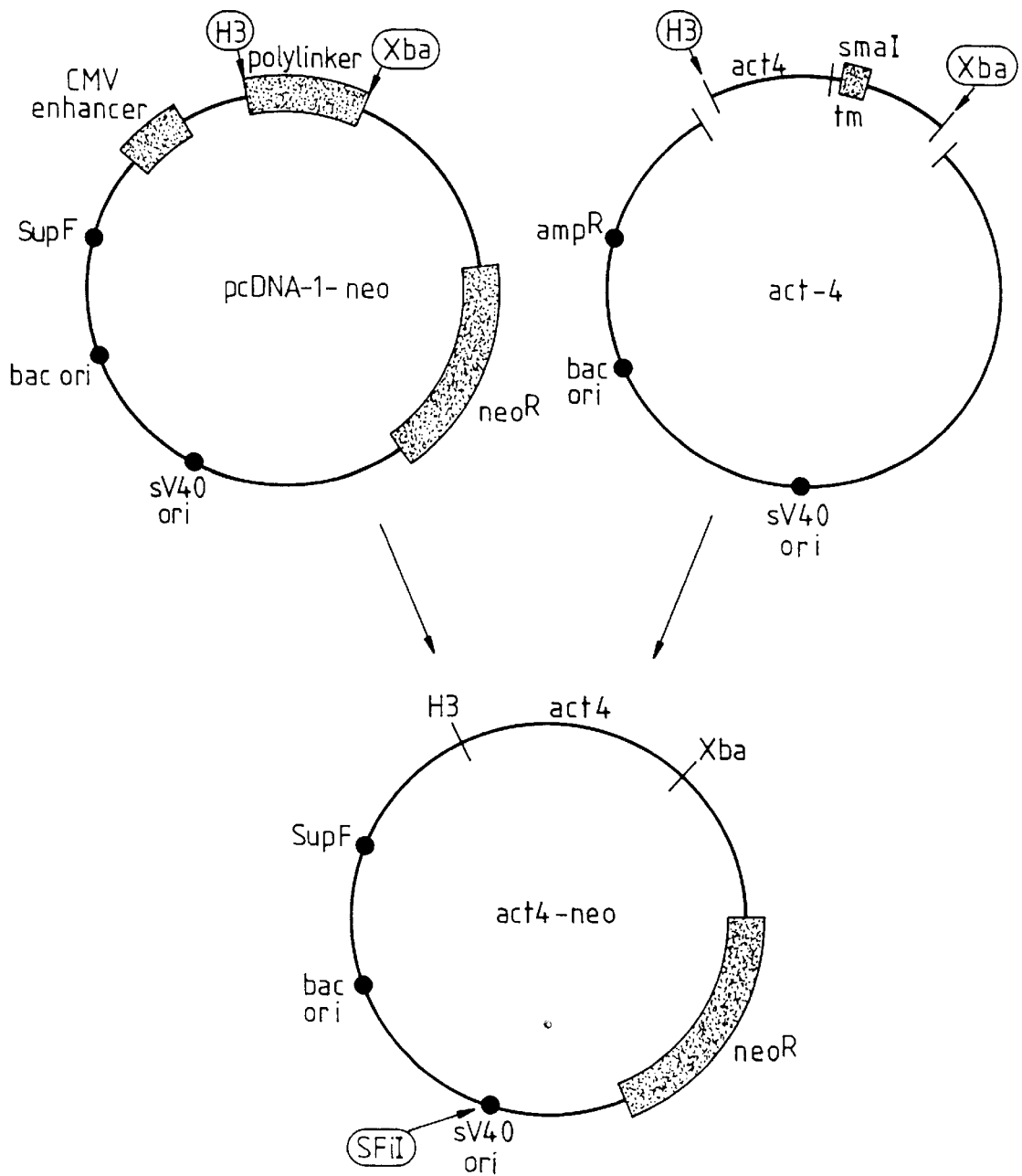

An XbaI-HindIII fragment was excised from the construct described in Example 4, and inserted into XbaI/HindIII-digested pcDNA-I-neo (Invitrogen) to generate an expression vector termed ACT-4-h-1-neo (FIG. 6). This vector was linearized with Sf1 and electroporated into three eukaryotic cell lines. These cell lines were SP2/O (a mouse myeloma derived from the Balb/c strain), Jurkat (a transformed human T-cell line) and COS-7 (an adherent monkey cell line). After a 48-h recovery period, transformed cells were selected in 1 mg/ml G418 (Gibco). After three weeks of selection, neo-resistant cell lines were incubated with a saturating concentration of L106 antibody, washed and overlayered onto 100 mm petri dishes coated with goat anti-mouse IgG to select for cells expressing ACT-4-h-1. After washing off unbound cells, adherent cells were recovered and expanded in tissue culture. Cell lines were subject to two further rounds of panning and expression. The resulting cell lines were shown by direct immunofluorescence staining to express abundant ACT-4-h-1 (FIG. 7).

The same strategy and principles are used to obtain a stable cell line expressing ACT-4-L-h-1 (See Example 10).

Example 7

Production of an ACT-4-h-1-Immunoglobulin Fusion Protein

Figure 8:
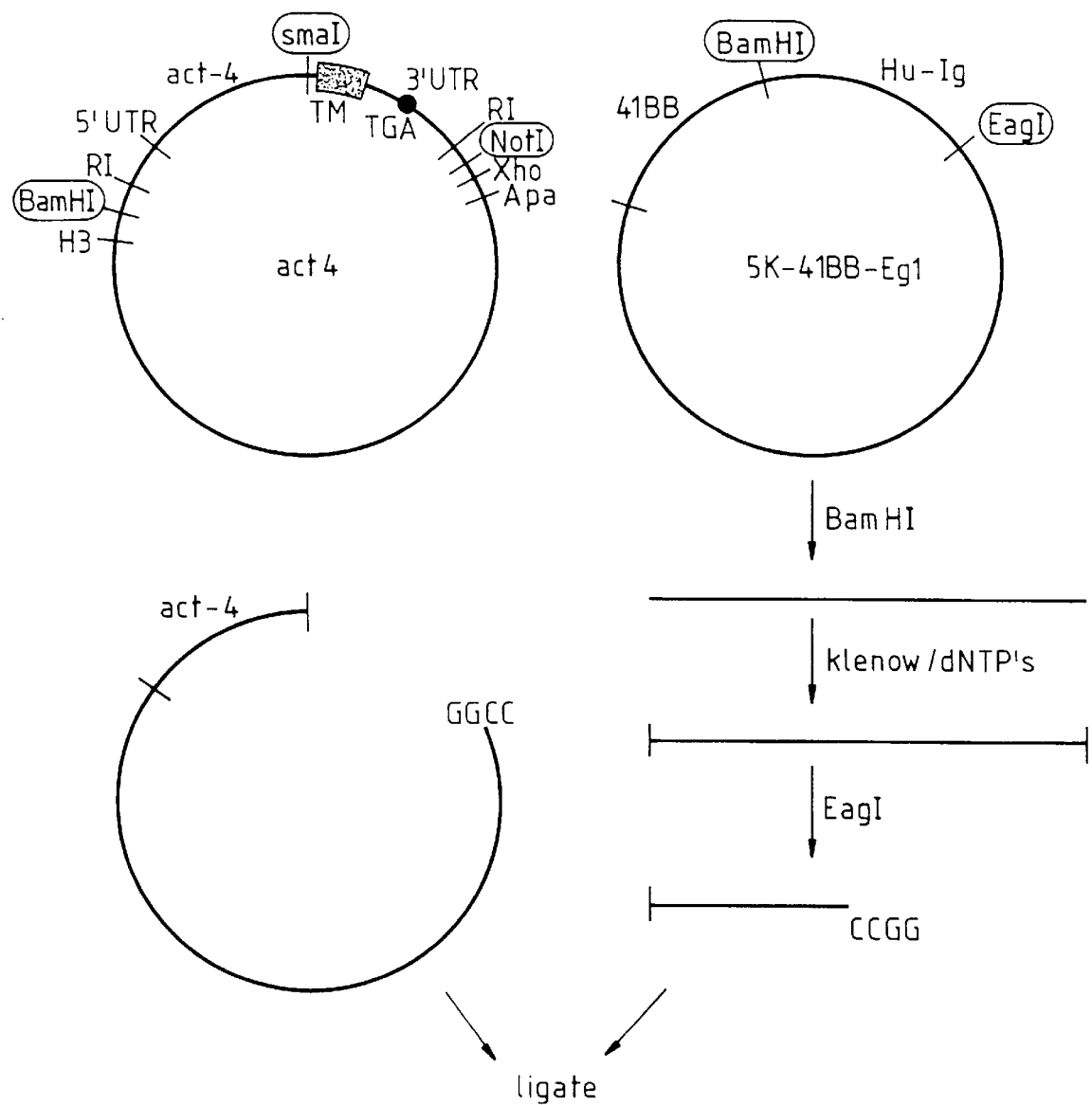

A soluble fusion protein has been constructed in which the extracellular domain of ACT-4-h-1 is linked via its C-terminal to the N-terminal of the constant domain of a human immunoglobulin. The vector encoding ACT-4-h-1 described in Example 4 was cleaved with SmaI and NotI to excise all ACT-4-h-1 sequences downstream of the SmaI site including the transmembrane, cytoplasmic and 3' untranslated regions. The remaining region encodes the soluble extracellular portion of ACT-4-h-1 (FIG. 8). The source of the immunoglobulin constant region to be joined to the ACT-4-h-1 extracellular domain was a plasmid termed 5K-41BB-Eg1 (*Proc. Natl. Acad. Sci. (USA)* 89: 10360–10364) (incorporated by reference for all purposes). This plasmid contains a 1.3 kb BamHI/EagI genomic fragment encoding the hinge, CH2 and terminal CH3 domains of human Ig, isotype gamma 1. The fragment required modification for insertion into the SmaI/NotI ends of the ACT-4-h-1 vector, while preserving the peptide reading frame across the SmaI junction to be formed by blunt-end ligation. The vector 5k-41BB-Eg1 was cut with BamHl and the resulting 5' extensions were filled with Klenow fragment. The vector was then cut with EagI releasing the 1.3 kb fragment with blunt and NotI compatible ends. This fragment was ligated with SmaI/NotI digested ACT-4-h-1 vector. The ligation mix was electroporated into *E. coli* and multiple transformant clones screened with PCR using ACT-4-h-1 and IgGI nucleotide fragments as primers.

Figure 9:
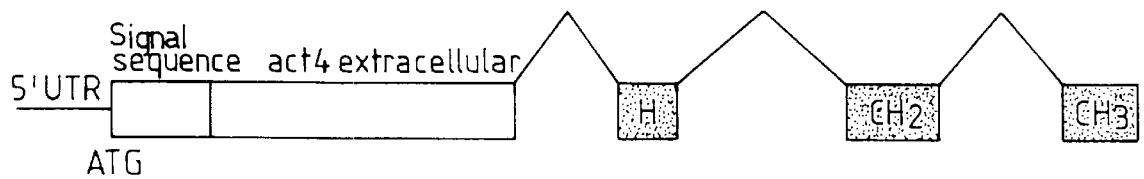

Plasmids containing the ACT-4-h-l-IgG1 coding were electroporated into COS cells. The cells were allowed to grow for five days at which point their supernatants were harvested and sterile filtered through a 0.2 micron membrane. The supernatants were tested for expression of ACT-4-h-1-IgG1 by dot blotting. Supernatants were blotted onto mitrocellulose and blocked with 5% nonfat dry milk. Replica blots were probed with antibody L106 or alkaline phosphatase-labelled goat anti-human immunoglobulin IgG (American Qualex). Antibody L106 was detected with an alkaline phosphatase labelled goat anti-mouse IgG. NBT/BCIP (Pierce) was used as a colorimetric substrate. High producing positive clones were sequenced at the junction site to confirm proper vector construction. The resulting fusion gene is depicted in FIG. 9.

Example 8

Identification of Cells Types Expressing a Ligand to ACT-4-h-1

Cell types expressing a ligand to ACT-4-h-1 were identified by indirect staining combined with flow cytometry using the ACT-4-h-1 recombinant immunoglobulin fusion protein described in Example 7 (hereinafter ACT-4-h-1-Rg) as a probe. Bound fusion protein was detected using phycoerythrin-conjugated anti-human Ig. These experiments revealed that a ligand to ACT-4-h-1 was expressed at low levels on a few B-cell lines, including a Burkitt lymphoma cell line (Jiyoye), and the EBV-transformed LCL's 9037, 9059, and MSAB. These cell lines scored 5% positive with a MCF of 3. See Table 2. With the cell line Jiyoye, it was possible to enrich for cells staining positive by the panning procedure to yield a cell line Jo-P5, which stained 90% positive with a MCF of 10. Other cell lines tested, including PBMC's and purified subpopulations of freshly isolated T-cells, B-cells, monocytes, dendritic cells, most T-cell tumor lines and myelomonocytic tumor cell lines, were substantially absent of a ligand to ACT-4-h-1. However, two HTLV-I infected T cell lines, HUT-102 and MT-2 expressed ACT-4-L-h-1, the latter at extremely high levels.

The experiment was repeated after activation of cells using either PHA or a combination of PMA/ionomycin. PBMC's activated with 2 μg/ml of PHA for three days stained between 2–10% positive for a ligand to ACT-4-h-1, depending on the donor. Activation of B-LCL cells and Burkit lymphoma lines using a combination of PMA (10 ng/ml) and ionomycin (500 ng/ml) induced substantial expression of ligand for some cell lines, particularly those such as MSAB that showed low levels of expression in the resting state. See Table 2. Unfractionated B cells also showed preferential expression of ligand (15% cells positive, MHC=5). Time course studies on MSAB cells indicated that ligand expression begins on day 2 following activation, and peaks on day 3 or 5. PMA/ionomycin-activation also induced preferential expression of ligand in erythroleukemia cell lines and in one of the three myelomonocytic cell lines tested, THP-1. PMA/ionomycin activation also induced a low level of expression of ligand in the T-cell lines but not in the other T-cell lines tested.

TABLE 2

Expression of Ligand to ACT-4-h-1 on Different Cell Types
TUMOR CELL LINE SCREEN

|  |  | Resting | Activated[1] |
|---|---|---|---|
| B-LCL | | | |
| | MSAB | 2–5%[2] mcf[3] 4 | 80% mcf 21 |
| | CESS | <2 | 70% mcf 25 |
| | JY | <2 | 40% 9 |
| | REM | <2 | 40% 11 |
| | 9059 | 2-5% mcf 4 | 40% 6 |
| | SKF | <2 | 30% 3 |
| | 9037 | 2-5% mcf 4 | 25% 5 |
| | 9062 | <2 | 10% 5 |
| | PGF | <2 | 6% 10 |
| | ARENT | <2 | 4% 5 |
| | KHY | <2 | 3% 5 |
| BURKIT LYMPHOMA | | | |
| | Jiyoye | 20% mcf 4 | 7% 5 |
| | Daudi | <2 | 10% 5 |
| | Naralwa | <2 | 5% 5 |
| | Raji | <2 | <2 |
| OTHER B CELL | | | |
| (Pre B) | NC-37 | <2 | <2 |
| (B-All) | SB | <2 | 15% 5 |
| T-CELL | | | |
| | HSB-2 | <2 | 6% 3 |
| | Jurkat | <2 | <2 |
| | Mol +4 | <2 | <2 |
| | Mol +3 | <2 | <2 |
| | HPB-ALL | <2 | |
| | HU +78 | <2 | <2 |
| | H9 | <2 | <2 |
| | VB | <2 | <2 |
| MYELO MONOCYTIC | | | |
| | THP-1 | <2 | 25% mcf 5 |
| | V937 | <2 | <2 |
| | HL60 | <2 | <2 |
| ERYTHRO LEUKEMIA | | | |
| | HEL | <2 | 25% 5 |
| | K562 | 2% | 25% 5 |
| HTLV-I INFECTED T-CELLS | | | |
| | HUT-102 | 30% mcf 4 | |
| | MT-2 | 100% 100 | |

[1]PMA/ionomycin
[2]% positive cells
[3]Mean channel fluorescence

Example 9

Cloning cDNA Encoding an ACT-4-h-1 Ligand

The cDNA clone for the ligand was isolated using a slightly modified COS cell expression system, first developed by Aruffo & Seed, supra. RNA was isolated from 72-hour PMA/ionomycin-activated human EBY-transformed B cells (cell line MSAB). Total RNA was extracted with TRI-reagent (Molecular Research Center), and poly(A)+RNA was isolated by oligo dT-magnetic bead purification (Promega). cDNA was synthesized by the method of Gubler & Hoffman, Gene 25:263–369 (1982) using superscript reverse transcriptase (Gibco/BRL) and an oligo dT primer. The blunted cDNA was ligated to non-self-complementary BstXl adaptors and passed over a Sephacryl S-500 column to remove unligated adaptors and small fragments (<300 base pairs). The Tinkered cDNA was then ligated into a BstXl cut eukaryotic expression vector, pcDNA (Invitrogen). The ligation products were precipitated, washed and electroporated into E. coli strain MC1061/P3 generating an unamplified library of 100 million independent clones. The average insert size in the library was 1 kb. The bulk of the library was amplified in 250 ml standard LB media. Plasmid DNA was recovered by alkaline lysis and purified over an ion-exchange column (Qiagen).

Sub-confluent COS-7 cells were transfected with the purified plasmid DNA by electroporation. Cells were plated on 100 mm dishes and allowed to grow for 48 hours. Cells were recovered from the plates with PBS-EDTA solution, incubated with monoclonal antibody ACT-4-h-1-Rg, and panned according to standard procedures. A second round panning numerous COS cells adsorbed to the plates showing enrichment for cells expressing ligand. Episomal DNA was recovered from the immunoselected cells by the Hirt method, and electroporated into bacteria for amplification.

Bacteria transformed with plasmid from the second round selection were cloned and amplified. DNA from individual clones was purified and tested for the ability to confer expression of a ligand to ACT-4-h-1 in COS-7 cells. Phycoerythrin-conjugated ACT-4-h-1-Rg was used to stain COS-7 cell monolayers and the cells were then examined by manual immunofluorescence microscopy. Clones #2, 26, and 30 gave high level expression of ACT-4-h-1-Rg binding activity.

Example 10

Sequence Analysis of a Ligand to ACT-4-h-1

The insert from clone 26 in Example 9 was subcloned into pBluescript at the HindIII and XbaI cloning sites. The clone was sequenced by the dideoxy chain termination method, using a T7 polymerase-based autoread sequencing kit (Pharmacia) on an ALF sequencer (Pharmacia). Three sub-clones were generated in pBluescript and were sequenced on both strands with M13 forward and universal primers. The cDNA and predicted amino acid sequences of clone 26 are shown in FIG. 10. The polypeptide formed by the predicted amino acid sequence is designated ACT-4-L-h-1.

The ACT-4-L-h-1 cDNA sequence contains 1079 base pairs, with a 137 bp 5' UTR and a 379 bp 3' UTR. An AATAAA polyadenylation signal is present at position 1024 followed by a 20 base poly A tail beginning at position 1049. Sequence analysis reveals a single open reading frame which encodes a 183 amino acid polypeptide, with a calculated molecular weight of 21,000. The open reading frame begins with the first ATG at position 149 and ends with a TGA at position 698. The ATG is flanked with a Kozak consensus initiation sequence with an A position at −3 and a G at +4. Hydrophobicity analysis reveals that the predicted amino acid sequence is that of a type II membrane protein with a single transmembrane domain of approximately 27 aa in the amino terminal portion of the protein. Also there are four N-linked glycosylation sites in the C-terminal portion of the molecule.

Comparison of the nucleotide sequence of ACT-4-L-h-1 with known sequences in the Genbank and EMBL databases reveals no significant homology to known genes except for a gene encoding a protein designated gp34 by Miura et al., Mol. Cell Biol. 11:1313–1325 (1991). The cDNA sequence of the coding region of the ACT-4-L-h-1 ligand is identical to that of gp34. However, the ACT-4-L-h-1 cDNA contained an additional 112 nucleotides at the 5' end compared with the gp34 sequence. Because the additional nucleotides occur within the 5' untranslated region, their presence is unlikely to alter the expression product. Most likely, the ACT-4-L-h-1 clone was derived from a more complete reverse transcript and is more representative of the in vivo 5' end. Possibly the extra sequence could be involved in regulating the translation of the protein.

Comparison of the predicted amino acid sequence of the ACT-4-L-h-1 ligand with known sequences in the Protein Information Resource (PIR) database using the FastDB program revealed an identity with gp34, and a very weak homology with TNF alpha. A secondary structure prediction algorithm developed by Chou & Fasman predicts that the ACT-4-L-h-1 ligand and TNF-alpha are both likely to form significant amounts of beta structures. This prediction is consistent with the observation that other members of the TNF family of proteins are all conformed or predicted to form beta jelly roll configurations rich in beta structures.

For the purposes of clarity and understanding, the invention has been described in these examples and the above disclosure in some detail. It will be apparent, however, that certain changes and modifications may be practiced within the scope of the appended claims. All publications and patent applications are hereby incorporated by reference in their entirety for all purposes to the same extent as if each were so individually denoted.

What is claimed is:

1. An isolated ACT-4 receptor polypeptide comprising an amino acid sequence selected from the group consisting of:
   (a) variants of the amino acid sequence of the ACT-4-h-1 receptor polypeptide shown in FIG. 5 (SEQ ID NO:2) having at least one conservative amino acid substitution; and
   (b) variants of the amino acid sequence of the ACT-4-h-1 receptor polypeptide shown in FIG. 5 (SEQ ID NO:2) which are encoded by a nucleic acid that hybridizes under stringent conditions to a nucleic acid encoding the amino acid sequence of the ACT-4-h-1 receptor polypeptide shown in FIG. 5 (SEQ ID NO:2),
   said isolated ACT-4 receptor polypeptides of (a) and (b) having the ability to bind specifically to the ACT-4-L-h-1 ligand having the amino acid sequence shown in FIG. 10 (SEQ ID NO:4).

2. The isolated ACT-4 receptor polypeptide of claim 1 that is human.

3. An isolated ACT-4 receptor soluble polypeptide comprising an amino acid sequence selected from the group consisting of:
   (a) variants of the amino acid sequence of the extracellular domain of the ACT-4-h-1 receptor polypeptide shown in FIG. 5 (SEQ ID NO:2) having at least one conservative amino acid substitution, wherein the extracellular domain of the ACT-4-h-1 receptor polypeptide shown in FIG. 5 (SEQ ID NO:2) has an amino terminus of any amino acid 1 to 25 of the amino acid sequence shown in FIG. 5 (SEQ ID NO:2) and a carboxyl terminus of amino acid 213 of the amino acid sequence shown in FIG. 5 (SEQ ID NO:2); and
   (b) variants of the amino acid sequence of said extracellular domain of the ACT-4-h-1 receptor polypeptide shown in FIG. 5 (SEQ ID NO:2) which are encoded by a nucleic acid that hybridizes under stringent conditions to a nucleic acid encoding the amino acid sequence of said extracellular domain of the ACT-4-h-1 receptor polypeptide shown in FIG. 5 (SEQ ID NO:2),
   said isolated ACT-4 receptor soluble polypeptides of (a) and (b) having the ability to bind specifically to the ACT-4-L-h-1 ligand having the amino acid sequence shown in FIG. 10 (SEQ ID NO:4).

4. The isolated ACT-4 receptor soluble polypeptide of claim 3 which is fused to a heterologous polypeptide.

5. The isolated ACT-4 receptor soluble polypeptide of claim 4 wherein the heterologous polypeptide is selected from the group consisting of a chromogenic enzyme, protein A, protein G, a FLAG protein, a toxin and a component of an immunoglobulin.

6. The isolated ACT-4 receptor soluble polypeptide of claim 4 wherein the heterologous polypeptide comprises a constant region domain of an immunoglobulin heavy chain.

* * * * *

UNITED STATES PATENT AND TRADEMARK OFFICE
CERTIFICATE OF CORRECTION

PATENT NO. : 6,156,878
DATED : December 5, 2000
INVENTOR(S) : Wayne Godfrey et al.

It is certified that error appears in the above-identified patent and that said Letters Patent is hereby corrected as shown below:

Column 1,
Line 13, insert: -- STATEMENT REGARDING FEDERALLY SPONSORED RESEARCH OR DEVELOPMENT
This invention was made with Government support under contract CA24607 awarded by the National Institutes of Health. The Government has certain rights in this invention. --

Signed and Sealed this

Sixteenth Day of October, 2001

Attest:

NICHOLAS P. GODICI
Attesting Officer
Acting Director of the United States Patent and Trademark Office

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
        (A) LENGTH: 1057 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 15..845

(xi) SEQUENCE DESCRIPTION: SEQ ID NO:1:

```
CAGCAGAGAC GAGG ATG TGC GTG GGG GCT CGG CGG CTG GGC CGC GGG CCG        50
              Met Cys Val Gly Ala Arg Arg Leu Gly Arg Gly Pro
                1               5                  10

TGT GCG GCT CTG CTC CTC CTG GGC CTG GGG CTG AGC ACC GTG ACG GGG        98
Cys Ala Ala Leu Leu Leu Leu Gly Leu Gly Leu Ser Thr Val Thr Gly
         15                  20                  25

CTC CAC TGT GTC GGG GAC ACC TAC CCC AGC AAC GAC CGG TGC TGC CAC       146
Leu His Cys Val Gly Asp Thr Tyr Pro Ser Asn Asp Arg Cys Cys His
     30                  35                  40

GAG TGC AGG CCA GGC AAC GGG ATG GTG AGC CGC TGC AGC CGC TCC CAG       194
Glu Cys Arg Pro Gly Asn Gly Met Val Ser Arg Cys Ser Arg Ser Gln
 45                  50                  55                  60

AAC ACG GTG TGC CGT CCG TGC GGG CCG GGC TTC TAC AAC GAC GTG GTC       242
Asn Thr Val Cys Arg Pro Cys Gly Pro Gly Phe Tyr Asn Asp Val Val
                 65                  70                  75

AGC TCC AAG CCG TGC AAG CCC TGC ACG TGG TGT AAC CTC AGA AGT GGG       290
Ser Ser Lys Pro Cys Lys Pro Cys Thr Trp Cys Asn Leu Arg Ser Gly
             80                  85                  90

AGT GAG CGG AAG CAG CTG TGC ACG GCC ACA CAG GAC ACA GTC TGC CGC       338
Ser Glu Arg Lys Gln Leu Cys Thr Ala Thr Gln Asp Thr Val Cys Arg
         95                 100                 105

TGC CGG GCG GGC ACC CAG CCC CTG GAC AGC TAC AAG CCT GGA GTT GAC       386
Cys Arg Ala Gly Thr Gln Pro Leu Asp Ser Tyr Lys Pro Gly Val Asp
    110                 115                 120

TGT GCC CCC TGC CCT CCA GGG CAC TTC TCC CCA GGC GAC AAC CAG GCC       434
Cys Ala Pro Cys Pro Pro Gly His Phe Ser Pro Gly Asp Asn Gln Ala
125                 130                 135                 140

TGC AAG CCC TGG ACC AAC TGC ACC TTG GCT GGG AAG CAC ACC CTG CAG       482
```

```
Cys Lys Pro Trp Thr Asn Cys Thr Leu Ala Gly Lys His Thr Leu Gln
                145                 150                 155
CCG GCC AGC AAT AGC TCG GAC GCA ATC TGT GAG GAC AGG GAC CCC CCA      530
Pro Ala Ser Asn Ser Ser Asp Ala Ile Cys Glu Asp Arg Asp Pro Pro
                160                 165                 170
GCC ACG CAG CCC CAG GAG ACC CAG GGC CCC CCG GCC AGG CCC ATC ACT      578
Ala Thr Gln Pro Gln Glu Thr Gln Gly Pro Pro Ala Arg Pro Ile Thr
                175                 180                 185
GTC CAG CCC ACT GAA GCC TGG CCC AGA ACC TCA CAG GGA CCC TCC ACC      626
Val Gln Pro Thr Glu Ala Trp Pro Arg Thr Ser Gln Gly Pro Ser Thr
                190                 195                 200
CGG CCC GTG GAG GTC CCC GGG GGC CGT GCG GTT GCC GCC ATC CTG GGC      674
Arg Pro Val Glu Val Pro Gly Gly Arg Ala Val Ala Ala Ile Leu Gly
205                 210                 215                 220
CTG GGC CTG GTG CTG GGG CTG CTG GGC CCC CTG GCC ATC CTG CTG GCC      722
Leu Gly Leu Val Leu Gly Leu Leu Gly Pro Leu Ala Ile Leu Leu Ala
                225                 230                 235
CTG TAC CTG CTC CGG AGG GAC CAG AGG CTG CCC CCC GAT GCC CAC AAG      770
Leu Tyr Leu Leu Arg Arg Asp Gln Arg Leu Pro Pro Asp Ala His Lys
                240                 245                 250
CCC CCT GGG GGA GGC AGT TTC CGG ACC CCC ATC CAA GAG GAG CAG GCC      818
Pro Pro Gly Gly Gly Ser Phe Arg Thr Pro Ile Gln Glu Glu Gln Ala
                255                 260                 265
GAC GCC CAC TCC ACC CTG GCC AAG ATC TGACCTGGGC CCACCAAGGT            865
Asp Ala His Ser Thr Leu Ala Lys Ile
                270                 275

GGACGCTGGG CCCCGCCAGG CTGGAGCCCG GAGGGTCTGC TGGGCGAGCA GGGCAGGTGC    925

AGGCCGCCTG CCCCGCCACG CTCCTGGGCC AACTCTGCAC CGTTCTAGGT GCCGATGGCT    985

GCCTCCGGCT CTCTGCTTAC GTATGCCATG CATACCTCCT GCCCCGCGGG ACCACAATAA   1045

AAACCTTGGC AG                                                       1057

(2) INFORMATION FOR SEQ ID NO:2:

(i) SEQUENCE CHARACTERISTICS:
        (A) LENGTH: 277 amino acids
        (B) TYPE: amino acid
        (D) TOPOLOGY: linear (ii) MOLECULE TYPE: protein (xi) SEQUENCE DESCRIPTION: SEQ ID NO:2:

Met Cys Val Gly Ala Arg Arg Leu Gly Arg Gly Pro Cys Ala Ala Leu
 1               5                  10                  15
Leu Leu Leu Gly Leu Gly Leu Ser Thr Val Thr Gly Leu His Cys Val
                20                  25                  30
Gly Asp Thr Tyr Pro Ser Asn Asp Arg Cys Cys His Glu Cys Arg Pro
                35                  40                  45
Gly Asn Gly Met Val Ser Arg Cys Ser Arg Ser Gln Asn Thr Val Cys
            50                  55                  60
Arg Pro Cys Gly Pro Gly Phe Tyr Asn Asp Val Val Ser Ser Lys Pro
65                  70                  75                  80
Cys Lys Pro Cys Thr Trp Cys Asn Leu Arg Ser Gly Ser Glu Arg Lys
                85                  90                  95
Gln Leu Cys Thr Ala Thr Gln Asp Thr Val Cys Arg Cys Arg Ala Gly
                100                 105                 110
Thr Gln Pro Leu Asp Ser Tyr Lys Pro Gly Val Asp Cys Ala Pro Cys
                115                 120                 125
```

```
Pro Pro Gly His Phe Ser Pro Gly Asp Asn Gln Ala Cys Lys Pro Trp
130                 135                 140

Thr Asn Cys Thr Leu Ala Gly Lys His Thr Leu Gln Pro Ala Ser Asn
145                 150                 155                 160

Ser Ser Asp Ala Ile Cys Glu Asp Arg Asp Pro Ala Thr Gln Pro
                165                 170                 175

Gln Glu Thr Gln Gly Pro Pro Ala Arg Pro Ile Thr Val Gln Pro Thr
            180                 185                 190

Glu Ala Trp Pro Arg Thr Ser Gln Gly Pro Ser Thr Arg Pro Val Glu
            195                 200                 205

Val Pro Gly Gly Arg Ala Val Ala Ala Ile Leu Gly Leu Gly Leu Val
            210                 215                 220

Leu Gly Leu Leu Gly Pro Leu Ala Ile Leu Leu Ala Leu Tyr Leu Leu
225                 230                 235                 240

Arg Arg Asp Gln Arg Leu Pro Pro Asp Ala His Lys Pro Pro Gly Gly
                245                 250                 255

Gly Ser Phe Arg Thr Pro Ile Gln Glu Glu Gln Ala Asp Ala His Ser
            260                 265                 270

Thr Leu Ala Lys Ile
        275
```

(2) INFORMATION FOR SEQ ID NO:3:

(i) SEQUENCE CHARACTERISTICS:
        (A) LENGTH: 1048 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 138..686

(xi) SEQUENCE DESCRIPTION: SEQ ID NO:3:

```
GGCCCTGGGA CCTTTGCCTA TTTTCTGATT GATAGGCTTT GTTTTGTCTT TACCTCCTTC      60

TTTCTGGGGA AAACTTCAGT TTTATCGCAC GTTCCCCTTT TCCATATCTT CATCTTCCCT     120

CTACCCAGAT TGTGAAG ATG GAA AGG GTC CAA CCC CTG GAA GAG AAT GTG        170
                   Met Glu Arg Val Gln Pro Leu Glu Glu Asn Val
                    1               5                   10

GGA AAT GCA GCC AGG CCA AGA TTC GAG AGG AAC AAG CTA TTG CTG GTG       218
Gly Asn Ala Ala Arg Pro Arg Phe Glu Arg Asn Lys Leu Leu Leu Val
            15                  20                  25

GCC TCT GTA ATT CAG GGA CTG GGG CTG CTC CTG TGC TTC ACC TAC ATC       266
Ala Ser Val Ile Gln Gly Leu Gly Leu Leu Leu Cys Phe Thr Tyr Ile
        30                  35                  40

TGC CTG CAC TTC TCT GCT CTT CAG GTA TCA CAT CGG TAT CCT CGA ATT       314
Cys Leu His Phe Ser Ala Leu Gln Val Ser His Arg Tyr Pro Arg Ile
    45                  50                  55

CAA AGT ATC AAA GTA CAA TTT ACC GAA TAT AAG AAG GAG AAA GGT TTC       362
Gln Ser Ile Lys Val Gln Phe Thr Glu Tyr Lys Lys Glu Lys Gly Phe
60                  65                  70                  75

ATC CTC ACT TCC CAA AAG GAG GAT GAA ATC ATG AAG GTG CAG AAC AAC       410
Ile Leu Thr Ser Gln Lys Glu Asp Glu Ile Met Lys Val Gln Asn Asn
                80                  85                  90

TCA GTC ATC ATC AAC TGT GAT GGG TTT TAT CTC ATC TCC CTG AAG GGC       458
Ser Val Ile Ile Asn Cys Asp Gly Phe Tyr Leu Ile Ser Leu Lys Gly
            95                  100                 105
```

```
TAC TTC TCC CAG GAA GTC AAC ATT AGC CTT CAT TAC CAG AAG GAT GAG          506
Tyr Phe Ser Gln Glu Val Asn Ile Ser Leu His Tyr Gln Lys Asp Glu
            110                 115                 120

GAG CCC CTC TTC CAA CTG AAG AAG GTC AGG TCT GTC AAC TCC TTG ATG          554
Glu Pro Leu Phe Gln Leu Lys Lys Val Arg Ser Val Asn Ser Leu Met
        125                 130                 135

GTG GCC TCT CTG ACT TAC AAA GAC AAA GTC TAC TTG AAT GTG ACC ACT          602
Val Ala Ser Leu Thr Tyr Lys Asp Lys Val Tyr Leu Asn Val Thr Thr
140                 145                 150                 155

GAC AAT ACC TCC CTG GAT GAC TTC CAT GTG AAT GGC GGA GAA CTG ATT          650
Asp Asn Thr Ser Leu Asp Asp Phe His Val Asn Gly Gly Glu Leu Ile
                160                 165                 170

CTT ATC CAT CAA AAT CCT GGT GAA TTC TGT GTC CTT TGAGGGGCTG               696
Leu Ile His Gln Asn Pro Gly Glu Phe Cys Val Leu
            175                 180

ATGGCAATAT CTAAAACCAG GCACCAGCAT GAACACCAAG CTGGGGGTGG ACAGGGCATG        756

GATTCTTCAT TGCAAGTGAA GGAGCCTCCC AGCTCAGCCA CGTGGGATGT GACAAGAAGC        816

AGATCCTGGC CCTCCCGCCC CCACCCCTCA GGGATATTTA AAACTTATTT TATATACCAG        876

TTAATCTTAT TTATCCTTAT ATTTTCTAAA TTGCCTAGCC GTCACACCCC AAGATTGCCT        936

TGAGCCTACT AGGCACCTTT GTGAGAAAGA AAAAATAGAT GCCTCTTCTT CAAGATGCAT        996

TGTTTCTATT GGTCAGGCAA TTGTCATAAT AAACTTATGT CATTGAAAAC GG              1048

(2) INFORMATION FOR SEQ ID NO:4:

(i) SEQUENCE CHARACTERISTICS:
        (A) LENGTH: 183 amino acids
        (B) TYPE: amino acid
        (D) TOPOLOGY: linear (ii) MOLECULE TYPE: protein (xi) SEQUENCE DESCRIPTION: SEQ ID NO:4:

Met Glu Arg Val Gln Pro Leu Glu Glu Asn Val Gly Asn Ala Ala Arg
 1               5                  10                  15

Pro Arg Phe Glu Arg Asn Lys Leu Leu Leu Val Ala Ser Val Ile Gln
            20                  25                  30

Gly Leu Gly Leu Leu Leu Cys Phe Thr Tyr Ile Cys Leu His Phe Ser
        35                  40                  45

Ala Leu Gln Val Ser His Arg Tyr Pro Arg Ile Gln Ser Ile Lys Val
    50                  55                  60

Gln Phe Thr Glu Tyr Lys Lys Glu Lys Gly Phe Ile Leu Thr Ser Gln
65                  70                  75                  80

Lys Glu Asp Glu Ile Met Lys Val Gln Asn Asn Ser Val Ile Ile Asn
                85                  90                  95

Cys Asp Gly Phe Tyr Leu Ile Ser Leu Lys Gly Tyr Phe Ser Gln Glu
            100                 105                 110

Val Asn Ile Ser Leu His Tyr Gln Lys Asp Glu Glu Pro Leu Phe Gln
        115                 120                 125

Leu Lys Lys Val Arg Ser Val Asn Ser Leu Met Val Ala Ser Leu Thr
    130                 135                 140

Tyr Lys Asp Lys Val Tyr Leu Asn Val Thr Thr Asp Asn Thr Ser Leu
145                 150                 155                 160
```

-continued

```
Asp Asp Phe His Val Asn Gly Gly Glu Leu Ile Leu Ile His Gln Asn
                165                 170                 175
Pro Gly Glu Phe Cys Val Leu
            180
```